US006825209B2

(12) United States Patent
Thomas et al.

(10) Patent No.: US 6,825,209 B2
(45) Date of Patent: Nov. 30, 2004

(54) COMPOUNDS HAVING UNIQUE CB1 RECEPTOR BINDING SELECTIVITY AND METHODS FOR THEIR PRODUCTION AND USE

(75) Inventors: Brian F. Thomas, Durham, NC (US); Herbert H. Seltzman, Raleigh, NC (US); Maria Elena Y. Francisco, Durham, NC (US)

(73) Assignee: Research Triangle Institute, Research Triangle Park, NC (US)

(*) Notice: Subject to any disclaimer, the term of this patent is extended or adjusted under 35 U.S.C. 154(b) by 0 days.

(21) Appl. No.: 10/121,708

(22) Filed: Apr. 15, 2002

(65) Prior Publication Data

US 2003/0199536 A1 Oct. 23, 2003

(51) Int. Cl.[7] .................. A61K 31/4745; C07D 471/06

(52) U.S. Cl. ...................... 514/285; 546/70; 548/374.1; 514/403; 514/406; 514/909

(58) Field of Search ............................... 514/285, 403, 514/406, 909; 546/70; 548/374.1

(56) References Cited

U.S. PATENT DOCUMENTS

| | | | |
|---|---|---|---|
| 5,596,106 A | 1/1997 | Cullinan et al. | |
| 5,747,524 A | 5/1998 | Cullinan et al. | |
| 5,783,402 A | 7/1998 | Konig et al. | |
| 6,509,367 B1 * | 1/2003 | Martin et al. | 514/406 |

FOREIGN PATENT DOCUMENTS

| | | |
|---|---|---|
| DE | 198 37 638 A1 | 2/2000 |
| EP | 0 656 354 A1 | 6/1995 |
| EP | 0 656 354 B1 | 6/1995 |
| EP | 0658546 A1 | 6/1995 |
| EP | 1 099 438 A2 | 5/2001 |
| EP | 1 099 439 A2 | 5/2001 |
| EP | 1 099 441 A2 | 5/2001 |
| JP | 2000-256190 | 9/2000 |
| WO | WO 96/02248 A1 | 2/1996 |
| WO | WO 97/19063 | 5/1997 |
| WO | WO97/21682 | 6/1997 |
| WO | WO98/32441 | 7/1998 |
| WO | WO99/02499 | 1/1999 |
| WO | WO99/24471 | 5/1999 |
| WO | WO 99/53917 | 10/1999 |
| WO | WO 99/609087 | 12/1999 |
| WO | WO 00/15609 | 3/2000 |
| WO | WO 00/46209 | 8/2000 |
| WO | WO00/46209 | 8/2000 |
| WO | WO01/04083 A1 | 1/2001 |
| WO | WO01/19807 A1 | 3/2001 |
| WO | WO01/32629 A1 | 5/2001 |
| WO | WO01/32663 A2 | 5/2001 |
| WO | WO01/58450 A2 | 8/2001 |
| WO | WO01-70700 A1 | 9/2001 |

OTHER PUBLICATIONS

Wiley, J.L. et al.: Novel Pyrazole cannabinoids: Insights into CB1 receptor recognition and activation. J. Pharmacol. Exp. Ther. vol. 296, pp. 1013–1022, 2001.*

Shim, J–Y. et al.: Molecular interaction of the antagonist N–(piperidin–1–yl)–5–(4–chlorophenyl)–1–(2, 4–dichlorophenyl)–4–methyl–1H–pyrazole–3–carboxamide with the CB1 cannabinoid recepror. J. Med. Chem. vol. 45, pp. 1447–1459, 2002.*

Abadji, et al., (R)–Methandamide: A Chiral Novel Anandamide Possessing Higher Potency and Metabolic Stability. J. Med. Chem. 37:1889–1893, 1994.

Aceto, et al., Cannabinoid precipitated withdrawal by the selective cannabinoid receptor antagonist, SR141716A. Eur. J. Pharmacol. 282:R1–R2, 1995.

Adams, et al., New analogs of tetrahydrocannabinol. XIX. J. Am. Chem. Soc. 71:1624–1628, 1949.

Adams, et al., Tetrahydrocannabinol homologs with double branched alkyl groups in the 3–position. XVUI. J. Am. Chem. Soc. 70:664–668, 1948.

Adams, et al., Assessment of anandamide interaction with the cannabinoid brain receptor: SR 141716A antagonism studies in mice and autoradiographic analysis of receptor binding in rat brain. J. Pharmacol. Exp. Ther. 284 (3): 1209–17, 1998.

Adkins, et al., A Synthesis of dl–Threonine. J. Am. Chem. Soc. 60: 1328–1331, 1938.

Ashton, et al., A regioselective route to 3–alkyl–1–aryl–1H–pyrazole–5–carboxylates: synthetic studies and structural assignments. J. Heterocycl. Chem. 30:307–311, 1993.

Barg, et al., Cannabinomimetic behavioral effects of and adenylate cyclase inhibior by new endogenous anandamides. Eur. J. Pharmacol. 287:145–152, 1995.

Barth, et al., Preparation of N–piperidino–5–(4–chlorophenyl)–1–2, 4–d–ichlorophenyl)–4–methylpyrazole–3–carboxamide. Eur. Pat. Appl.: EP–94–402717, 12 pp., 1995a. Also published as EP0656354.

Bayewitch, et al., The peripheral cannabinoid receptor: adenylate cyclase inhibition and G protein coupling, FEBS Lett. 375:143–7, 1995.

Beardsley, et al., Studies on the agonistic activity of .DELTA..sup.9,11–THC in mice, dogs and rhesus monkeys and its interactions with delta 9–tetrahydrocannabinol. J. Pharmacol. exp. Ther. 241:521–6, 1987.

(List continued on next page.)

*Primary Examiner*—Charanjit S. Aulakh
(74) *Attorney, Agent, or Firm*—Oblon, Spivak, McClelland, Maier & Neustadt, P.C.

(57) ABSTRACT

Compounds are provided that are amide analogs of SR141716A having unique CB1 receptor selectivity and providing WIN sparing binding characteristics, pharmaceutical compositions containing the compounds and their use in a method of treatment of CB1 receptor related disorders, such as obesity, schizophrenia, memory dysfunction and marijuana abuse.

22 Claims, 7 Drawing Sheets

OTHER PUBLICATIONS

Begley, et al., Pyrazolo[1,5–f]phenanthridine and Derivatives: Electrochemical and Photochemical Synthesis. Journal of the Chemical Society, Perkin Transactions 1 1974: 2633–2637, 1974.

Blomquist, and Baldwin: J. Am. Chem. Soc. 70: 29, 19.

Borch, et al., The cyanohydridoborate anion as a selective reducing agent. J. Am. Chem. Soc. 93:2897–2904, 1971.

Breivogel, et al., Evidence for a new G protein–coupled cannabinoid receptor in mouse brain. Mol. Pharmacol. 60 (1):155–63., 2001.

Brown, C. A.: Facile Reaction of potassium hydride with ketones. Rapid quantitative formation of potassium enolates from ketones via kaliation. J. Org. Chem. 39:1324, 1974.

Carpino, et al., Oxidative reactions of hydrazines. V. Synthesis of Monobenzyl 1,1–Disubstituted Hydrazines and 2–Amino–2,3–dihydro–1H–benz[de]isoquinoline. J. Am. Chem. Soc., 82: 2728–2731, 1960.

Chen, J. P., et al., .quadrature.9–THC produces naloxone–blockable enhancement of presynaptic basal dopamine efflux in nucleus accumbens of conscious, freely–moving rats as measured by intracerebral microdialysis. Psychopharmacology 102:156–62, 1990.

Chen, J., et al., Ventral tegmental microinjection of .DELTA..sup.9–THC enhances ventral tegmental somatodendritic dopamine levels but not forebrain dopamine levels: evidence for local neural action by marijuana's psychoactive ingredient. Brain Res. 621:65–70, 1993.

Childers, et al., Role of cyclic AMP in the actions of cannabinoid receptors. Biochem. Pharmacol. 52:819–27, 1996.

Collins, et al., Prevention by the cannabinoid antagonist, SR141716A, of the cannabinoid–mediated blockade of long–term potentiation in the rat hippocampal slice. Brit. J. Pharmacol. 115:869–870, 1995.

Compton, et al., Synthesis and pharmacological evaluation of ether and related analogues of .DELTA..sup.8–, .DELTA..sup.9, and .DELTA..sup.9,11–tetrahydrocannabinol. J. Med. Chem. 34:3310–3316, 1991.

Compton, et al., Aminoalkylindole analogs: cannabimimetic activity of a class of compounds structurally distinct from .DELTA..sup.9–THC. J. Pharmacol. Exp. Ther. 263:1118–1126, 1992.

Compton, et al., Cannabinoid structure–activity relationships: correlation of receptor binding and in vivo activities. J. Pharmacol. Exp. Ther. 265:218–26, 1993.

Compton, et al., In vivo characterization of a specific cannabinoid receptor antagonist (SR141716A) inhibition of .DELTA..sup.9–THC–induced responses and apparent agonist activity. J. Pharmacol. Exp. Ther. 277:586–594, 1996.

Connors, et al., A theoretical investigation of the pyrazole phototransposition. J. Org. Chem. 56:6321 1991.

Cramer, Richard D. III.: Partial Least Squares (PLS): Its strengths and limitations. In: Perspectives in Drug Design, ESCOM, Leiden, pp. 269–277, 19.

Cullinan, et al., Benzo[b]furan and benzo[b]thiophene derivatives useful as cannabinoid receptor antagonists. In U.S., pp. 13 pp. Cont.–in–part of U.S. Ser. No. 275,895, abandoned., (Eli Lilly and Company, USA)., US, 1997. Corresponds to U.S. 5,747,524.

Deutsch, et al., Enzymatic synthesis and degradation of anandamide, a cannabinoid receptor agonist. Biochem. Pharmacol. 46:791–796, 1993.

Devane, et al., Determination and characterization of a cannabinoid receptor in rat brain. Mol. Pharmacol., 34:605–613, 1988.

Devane, et al., A novel probe for the cannabinoid receptor. J. Med. Chem. 35(11):2065–9, 1992b.

Dewey, W. L.: Cannabinoid pharmacology. Pharmacol. Rev. 38:151–78, 1986.

Dewey, et al., The effect of various neurohumoral modulators on the activity of morphine and the narcotic antagonists in the tail–flick and phenylquinone tests, J. Pharmacol. Exp. Ther. 175:435–442, 1970.

Dewey, W. L. and Harris, L. S.: Antinociceptive activity of the narcotic antagonist analgesics and antagonistic activity of narcotic analgesics in rodents, J. Pharmacol. Exp. Ther. 179:652–659, 1971.

Di Marzo, et al., Palmitoylethanolamide inhibits the expression of fatty acid aamide hydrolase and enhances the antiproliferative effect of anandamide in human breast cancer cells. Biochem. J. 358: 249–55., 2001.

Drummond, et al., J. Med. Chem. 32 (9): 2116–2128, 1989.

Dutta, et al., The synthesis and pharmacological evaluation of the cannabinoid antagonist SR141716A. Med. Chem. Res. 5:54–62, 1995.

Eissenstat, et al., Aminoalkylindoles: structure–activity relationships of novel cannabinoid mimetics. J. Med. Chem. 38:3094–105, 1995.

Felder, et al., Comparison of the pharmacology and signal transduction of the human cannabinoid CB1 and CB2 receptors. Mol. Pharmacol., 48:443–450, 1995.

Fernando, et al., Structure–activity relationships of some novel analogues of SR141716A. International Cannabis Research Society abstract, 1996.

Fong, et al., The role of histidine 265 in antagonist binding to the neurokinin–1 receptor. J. Biol. Chem. 269:2728–2732, 1994.

Galiegue, et al., Expression of central and peripheral cannabinoid receptors in human immune tissues and leukocyte subpopulations. Eur. J. Biochem. 232:54–61, 1995.

Gatley, et al., [.sup.1231]–labeled AM251: a radioligand which binds in vivo to mouse brain cannabinoid CB1 receptors. Eur. J. Pharmacol. 307:331–338, 1996.

Ghali, et al., A High–Yielding Synthesis of Monoalkyl Hydrazines. J. Org. Chem., 46:5413–5414, 1981.

Gold, et al., A comparison of the discriminative stimulus properties of .DELTA..sup.9–THC and CP 55,940 in rats and rhesus monkeys. J. Pharmacol. Exp. Ther. 262:479–486, 1992.

Grimshaw, et al., Electrochemical reactions. Par 25. A comparison of the reductive and photochemical cyclization of some i–(2–chlorophenyl)–j–phenyltriazoles. Proc. R. Jr. Acad., Sect. B 83 B (1–16): 93–101, 1983.

Guo, Y., et al., (—)–11–Hydroxy–7'–isothiocyanato–1', 1'–dimethylheptyl.DE–LTA..sup.8–THC: A novel, high affinity cannabinoid receptor in the brain. J. Med. Chem. 37(23):3867–70, 1994.

Han, Y., and Hu, H.: Synthesis 1990: 122, 1990.

Herkenham, M., et al. Cannabinoid receptor localization in brain. Proc. Natl. Acad. Sci. 87:1932–1936, 1990.

Herkenham, M.: Canabinoid receptor localization in brain: relationship to motor and reward systems. Ann. N.Y. Acad. Sci. 654:19–32, 1992.

Hiltunen, A. J. and Jarbe, T. U.: Cannabidiol attenutates.DELTA..sup.9–THC–like discriminative stimulus effects of cannabinol. Eur. J. Pharmacol. 125:301–304, 1986.

Hirst, R. A., Almond, S. L. and Lambert, D. G.: Characterisation of the rat cerebella CB1 receptor using SR141716A, a central cannabinoid receptor antagonist. Neurosci. Lett. 220:101–104, 1996.

Houston, D. B., Lan, R., Pigg, J. J., Wilken, G., Howlett, A. C. and Makriyannis, A.: Structure–activity relationship of pyrazole compounds to CB1 receptor affinity and function. International Cannabis Research Society abstract to be presented Jun., 1997.

Howlett, A. C., Johnson, M. R., Melvin, L. S. and Milne, G. M.: Nonclassical cannabinoid analgetics inhibit adenylate cyclase: development of a cannabinoid receptor model. Mol. Pharmacol. 33:297–302, 1988.

Huestis, M. A., Gorelick, D. A., Heishman, S. J., Preston, K. L., Nelson R. A. Moolchan, E. T., and Frank, R. A.: Blockade of effects of smoked marijuana by the CB1–sleective cannabioid receptor antagonist SR141716. Arch. Gen. Psychiatry 58 (4): 322–8., 2001.

Huffman, J. W., Yu, S., Showalter, V., Abood, M. E., Wiley, J. W., Compton, D. R., Martin, B. R., Ramblett, R. D. And, Reggios, P. H.: Synthesis and pharmacology by very potent cannabinoid lacking a phenolic hydroxyl with high affinity for the CB2 receptor. J. Med. Chem. 39(90):3875–3877, 1996.

Hunter, T. R., Mericle, J. M., Patel, M. J. and Reggio, P. H. The aminoalylindole binding site at the cannabinoid CB1 and CB2 receptors. International Cannabis Research Society abstract, 1996.

Iorio, M. A., and Landi–Vittory, R.: Farnaco Ed. Sci. 18:453–464, 1963.

Ishac, E. J., Jiang, L., Lake, K. D., Varga, K., Abood, M. E. and Kunos, G.: Inhibition of exocytotic noradrenaline release by presynaptic cannabinoid CB1 receptors on peripheral sympathetic nerves. Br. J. Pharmacol. 118:2023–8, 1996.

Jansen, E. M., Haycock, D. A., Ward, S. J. and Seybold, V. S.: Distribution of cannabinoid receptors in rat brain determined with aminoalkylindoles. Brain Res. 575:93–102, 1992.

Johnson, M. R. and Melvin. L. S. The discovery of nonclassical cannabinoid analgetics. in Cannabinoids as Therapeutic Agents, CRC Press, Boca Raton, Fal., pp. 121–145, 1986.

Jones, R. G. and. Gilman, H.: The halogen–metal interconversion reaction with organolithium compounds. Organic Reactions 6, ch. 7, 339, 1951.

Jung, M. E., and Hatfield, G. L.: Tetrahedron Lett.: 4483, 1978.

Kang, H.–Y., and Song, S.–E.: Tetrahedron Lett. 41: 937–939, 2000.

Keimowitz, A. R., Martin, B. R., Razdan, R.K., Crocker, P. J., Mascarella, S. W., and Thomas, B. F.: QSAR analysis of .DELTA..sup.8–THC analogues: relationship of side–chain conformation to cannabinoid receptor affinity and pharmacological potency. J. Med. Chem. 43 (1): 59–70., 2000.

Kenakin, T.: Pharmacologic Analysis of Drug Receptor Interaction, Raven Press, New York, pp. 324, 1993.

Kenakin, T. The classification of seven transmembrane receptors in recombinant expression systems. Pharmacol. Rev. 48:413–463.

Kornetsky, C.: Brain–stimulation reward: a model for the neuronal bases for drug–induced euphoria. NIDA Res. Monogr. 62:30–50, 1985.

Kuster, J. E., Stevenson, J. I., Ward, S. J., D'Ambra, T. E. and Haycock, D. A.: Aminoalkylindole binding in rat cerebellum: selective displacement by natural and synthetic cannabinoids. J. Pharmacol. Exp. Ther. 264:1352–1363, 1993.

Lallemand, F., Soubrie, P. H., and De Witte, P. H.: Effects of CB1 cannabinoid receptor blockade on ethanol preference after chronic ethanol administration. Alcohol Clin Exp Res 25 (9): 1317 23, 2001.

Lan, R., Liu Q., Fan, P., Lin, S., Fernando, S. R., McCallion, D., Pertwee, R., and Makriyannis, A.: Structure–activity relationships of pyrazole derivatives as cannabinoid receptor antagonists. Journal of Medicinal Chemistry 42(4): 769–776, 1999.

Ledent, C., Valverde, O., Cossu, G., Petitet, F., Aubert, J. F., Beslot, F., Bohme, G. A., Imperato, A., Pedrazzini, T., Roques, B.P., Vassart, G., Fratfa, W., and Parmenter, M.: Unresponsiveness to cannabinoids and reduced addictive effects of opiates in CB1 receptor knockout mice. Science 283 (5400): 401–4., 1999.

Lee, II. B., and Balasubramanian, S.: Solid Phase Synthesis of N–Alkyl–N–(beta–keto)amides and 1,2,4,5–Tetrasubstituted Imidazoles Using a Traceless Cleavage Strategy. Org. Lett. 2(3): 323–326, 2000.

Le Fur, G., Arnon, M., Rinaldi–Carmoni, M., Barth, F. and Heshmati, H.: SR141716A, a selective antagonist of CB1 receptors and obesity. presented at the 2001 meeting of the international Cannabinoid Research Society, Madrid, Spain, 2001.

Lee, R. A., McAndrews, C., Patel, K. M., and Reusch, W.: Tetrahedron Lett. 965, 1973.

Lichtman, A.H., Dimen, K.R. and Martin, B.R.: Systemic or intrahippocampal cannabinoid administration impairs spatial memory in rats. Psychopharmacology 119:282–90, 1995.

Lichtman, A. H. and Martin, B. R.: .DELTA..sup.9–THC impairs spatial memory through a cannabinoid receptor mechanism. Psychopharmacology. 126:125–131, 1996.

Lynn, A.B. and Herkenham, M.: Localization of cannabinoid receptors and nonsaturable high–density cannabinoid binding sites in peripheral tissues of the rat: implications for receptor–mediated immune modulation by cannabinoids. J. Pharmacol. Exp. Ther. 268–1612–23, 1994.

Mansbach, R. S., Roveti, C. C., Winston, E. N. and Lowe, J. A. In: Effects of the cannabinoid CB1 receptor antagonist SR141716A on the behavior of pigeons and rats. Psychopharmacology 124:315–322, 1996.

Martin, B. R.: Cellular effects of cannabinoids. Pharmacol. Rev. 38:45–74, 1986.

Martin, B. R., Compton, D. R., Semus, S. F., Lin, S., Marciniak, G., Grzybowska, J., Charalambous, A. and Makriyannis, A.: Pharmacological evaluation of iodo and nitro analogs of .DELTA..sup.8–THC and .DELTA..sup.9–THC. Pharmacol. Biochem. Behav. 46:295–301, 1993.

Matsuda, L. A., Lolait, S. J., Brownstein, M. J., Young, A. C. and Bonner, T. I.: Structure of a cannabinoid receptor and functional expression of the cloned cDNA [see comments]. Nature 346:561–4, 1990.

McIlwain, and Richardson: Biochemical Journal 33: 45, 1939.

Mechoulam, R., Shani, A., Ederly, H. Grumfeld, Y.: Chemical basis of hashishactivity. Science, 169:611, 1970.

Munro, S., Thomas, K. L. and Abu–Shaar, M.: Molecular characterization of a peripheral receptor for cannabinoids. Nature 365:61–65, 1993.

Munson, P. J. and Rodbard, D.: Ligand: A versatile computerized approach for characterization of ligand–binding systems. Anal. Biochem. 107:220–239, 1980.

Murray, W. V. and Wachter, M. P.: A simple regioelective synthesis of ethyl 1,5–diarylpyrazole–3–carboxylates. J. Heterocycl. Chem. 26:1389–1392, 1989.

Negishi, E., King, A. O., and Okukado, N.: Selective Carbon–Carbon Bond Formation via Transition Metal Catalysis. 3. A highly Selective Synthesis of Unsymmetrical Biaryls and Diarylmethanes by the Nickel–or Palladium–Catalyzed Reaction of Aryl– and Benzylzine Derivatives with Aryl Halides. J. Org. Chem. 42: 1821–1823, 1977.

Ng Cheong Ton, J.M., Gerhardt, G. A., Friedemann, M., Etgen, A. M., Rose, G. M., Sharpless, N. S., and Gardner, E. L.: The effects of .DELTA..sup.9–THC on potassium–evoked release of dopamine in the rat caudate nucleus: an in vivo electrochemical and in vivo microdialysis study. Brain Res. 451:59–68, 1988.

Nicklaus, M. C., Wang, S., Driscoll, J. S. and Milne, G. W.: Conformational changes of small molecules binding to proteins. Bioorg. Med. Chem. 3:411–428. 1995.

Nowell, K. W., Pettit, D. A., Cabral, W. A., Zimmerman, H. W., Jr., Abood, M. E., and Cabral, G. A.: High–level expression of the human CB2 cannabinoid receptor using a baculovirus system. Biochem Pharmacol 55: 1893–905, 1998.

Onaivi, E. S., Green, M. R. and Martin, B. R.: Pharmacological characterization of cannabinoids in the elevated plus maze. J. Pharmacol. Exp. Ther. 253:1002–1009, 1990.

Pacheco, M., Childers, S. R., Arnold, R., Casiano, F. and Ward, S. J.: Aminoalkylindoles: actions on specific G–protein–linked receptors. J. Pharmacol. Exp. Ther. 257:170–83, 1991.

Pacheco, M. A., Ward, S. J., and Childers, S. R.: Differential requirements of sodium for coupling of cannabinoid receptors to adenylyl cyclase in rat brain membranes. J. Neurochem. 62:1773–1787, 1994.

Pavlik, J. W., Connors, R. E., Burns, D. S., and Kurzweil, E. M.: Phototransposition chemistry of 1–phenylpyrazole. Experimental and computational studies. J. Am. Chem. Soc. 115:7645–52, 1993.

Pavlik, J. W., and Kurzweil, E. M.: Phototransposition chemistry of 1–methylpyrazole. uterium, methyl, and fluorine substitution. J. Org. Chem. 56:6313–20, 1991.

Pertwee, R. G.: The ring test: A quantitative method for assessing the 'cataleptic' effect of cannabis in mice, Br. J. Pharmacol., 46:753–763, 1972.

Pertwee, R. G., Stevenson. L. A., Elrick, D. B., Mechoulam, R. and Corbett, A. D.: Inhibitory effects of certain enantiomeric cannabinoids in the mouse vas deferens and the myenteric plexus preparation of gunea–pig small intestine, B. J. Pharmacol. 105:980–984, 1992.

Pertwee, R. G.: Stevenson. L. A. and Griffin, G.: Cross–tolerance Between .DELTA..sup.9–THC and the Cannabimimetic Agents CP 55,940, WIN 55,212–2 and Anandainide, Br. J. Pharmacol. 110:1483–1490, 1993.

Pertwee, R. G. and Griffin, G.: A preliminary investigation of the mechanisms underlying cannabinoid tolerance in the mouse vas deferens. Eur. J. Pharmacol. 272:67–72, 1995.

Pertwee, R. G., Griffin, G., Fernando, S., Li, X., Hill, A. and Makriyannis, A.: AM630, a competitive cannabinoid receptor antagonist. Life Sci. 56:1949–1955, 1995a.

Pertwee, R. G.: Pharmacological, physiological and clinical implications of the discovery of cannabinoid receptors: an overview. In: Cannabinoid Receptors (R. Pertwee, ed.), Academic Press, New York, N.Y., pp. 1–34, 1995b.

Pertwee, R. G., Griffin, G., Lainton, J. A. and Huffman, J. W.: Pharmacological characterization of three novel cannabinoid receptor agonists in the mouse isolated vas deferens. Eur J Pharmacol 284:241–7, 1995c.

Pertwee, R. G., Fernando, S. R., Griffin, G., Abadji, V. and Makriyannis, A.: Effect of phenylmethylsulphonyl fluoride on the potency of anandamide as an inhibitor of electrically evoked contractions in two isolated tissue preparations. Eur. J. Pharmacol. 272:73–78, 1995d.

Pertwee, R. G., Fernando, S. R., Nash, J. E. and Coutts, A. A.: Further evidence for the presence of cannabinoid CB1 receptors in guinea–pig small intestine. Br. J. Pharmacol. 118:2199–2205, 1996.

Pertwee, R. G. and Fernando, S. R.: Evidence for the presence of cannabinoid CB1 receptors in mouse urinary bladder. Br. J. Pharmacol. 118;2053–2058, 1996.

Petitet, F., Marin, L. and Doble, A.: Biochemical and pharmacological characterization of cannabinoid binding sites using [.sup.3H]SR141716A. Neuroreport 7:789–792, 1996.

Poling, J. S., Rogawski, M. A., Salem, N. and Vicini, S.: Anandamide, an endogenous cannabinoid, inhibits Shaker-related voltage–gated K.sup.+ channels. Neuropharmacology 35:983–991, 1996.

Rambaud, M., Bakasse, M., Duguay, G., and Villieras, J.: A one–step synthesis of alkyl 2–oxo–3–alkenoates from alkenyl Grignard reagents and dialkyl oxalates. Synthesis 564–566, 1988.

Razdan, R. K.: Structure–activity relationships in cannabinoids. Pharmacol. Rev. 38:75–149, 1986.

Reggio, P. H., McGaughey, G. B., Odear, D. F., Seltzman, H. H., Compton, D: and Martin, B. R.: A rational search for the separation of psychoactivity and analgesia in cannabinoids. Pharmacol. Biochem. Behav. 40:479–86, 1991.

Reggio P. H. Panu, A. M. and Miles, S.: Characterization of a region of steric interference at the cannabinoid receptor using the active analog approach. J. Med. Chem. 36:1761–71, 1993.

Reggio, P. H., Bramblett, R. D., Yuknavich, H., Seltzman, H. H., Fleming, D. N., Fernando, S. R., Stevenson, L. A. and Pertwee, R. G.: The design, synthesis and testing of desoxy–CBD: further evidence for a region of steric interference at the cannabinoid receptor. Life Sci 56:2025–32, 1995.

Reggio, P.H.: Ligand–ligand and ligand–receptor approaches to modeling the cannabinoid CB1 and CB2 receptors: achievements and challenges. Curr. Med. Chem. 6:665–83, 1999.

Richardson, J. D., Aanonsen, L. and Hargreaves. K. M.: SR 141716A, a cannabinoid receptor antagonist, produces hyperalgesia in untreated mice. Eur. J. Pharmacol. 319:R3–4, 1997.

Rinaldi–Carmona, M., Barth, F., Heaulme, M., Shire, D., Calandra, B., Congy, C., Martinez, S., Maruani, J., Neliat, G., Caput, D. et al: SR141716A, a potent and selective antagonist of the brain cannabinoid receptor. FEBS Lett. 350:240–244, 1994.

Rinaldi–Carmona, M., Barth, F., Heaulme, M., Alonso, R., Shire, D., Congy, C., Soubrie, P., Breliere, J. C. and Le Fur, G.: Biochemical and pharmacological characterisation of SR141716A, the first potent and selective brain cannabinoid receptor antagonist. Life Sci. 56:1941–1947, 1995a.

Rinaldi–Carmona, M., Barth, F., Millan, J., Derocq, J.–M. Casellas, P., Congy, C., Oustric, D., Sarran, M., Bouaboula, M., Calandra, B., Portier, M., Shire, D., Breliere, J.–C. and Le Fur, G.: SR 144528, the first potent and selective antagonist of the CB2 cannabinoid receptor. J. Pharmacol. Exp. Ther. 284: 644–650, 1998.

Ronald, R. C. and Lansinger, J. M.: Total synthesis of frustulosin. J. Chem. Soc., Chem. Commun. 124, 1979.

Rubino, T., Massi, P., Vigano, D., Fuzio, D., and Parolaro, D.: Long–term treatment with SR141716A, the CB1 receptor antagonist, influences morphine withdrawal syndrome. Life Sci 66 (22): 2213–9., 2000.

Sanudo–Pena, M. C., Tsou, K., Delay, E. R. Hohman, A. G., Force, M and Walker, J. M.: Endogenous cannabinoids as an aversive or counter–rewarding system in the rat [In Process Citation]. Neurosci. Lett., 223:125–128, 1997.

Sarshar, S., Siev, D., and Mjalli, A. M. M.: Imidazole libraries on solid support. Tet. Lett. 37:835–838, 1996.

Schatz, A. R., Lee, M., Condie, R. B., Pulaski, J. T. and Kaminski, N. E.: Cannabinoid receptors CB1 and CB2: a characterization of expression and adenylate cyclase modulation within the immune system. Tox. App. Pharmacol. 142:278–287, 1997.

Schmid, P. C., Paria, B. C., Kerbsbach, R. J., Schmid, H. H, O. and Dey, S. K. Changes in anandamide levels in mouse uterus are associated with uterine receptivity for embryo implantation. Proc. Natl. Acad. Sci. USA 94:4188–92, 1997.

Selley, D. E., Stark, S., Sim, L. J. and Childers, S. R.: Cannabinoid receptor stimulation of guanosine–5'–O–(3–[.sup.35S]thio)trip–hosphate binding in rat brain membranes. Life Sci. 59:659–68, 1996.

Seltzman, H. H., Setzer, S. R., Williams, D. L., Demian, I., Wyrick, C. D. and Pitt, C. G.: Syntheses of cannabinoid radioligands and haptens for use in radioimmunoassay and receptor site studies. In: Marihuana '84–Proceedings of the Oxford Symposium on Cannabis (D. J. Harvey, ed.), IRL Press, Oxford and Washington, D.D., p. 183, 1985.

Seltzman, H. H., Hsieh, Y.–A., Pitt, C.G. and Reggio, P. H.: Synthesis of rotationally restricted tetrahydrocannabinol ethers. J. Org. Chem. 56:1549, 1991.

Seltzman, H. H., Moody, M. A. and Begum, M. K.: Allylic substitution/rearrangement of cannabinoids with trimethylsilyl bromide. Tetrahedron Lett. 33:3443, 1992.

Seltzman, H H., Carroll, F. I., Burgess, J. P. Wyrick, C. D. and Burch, D. F.: Synthesis, spectral studies and tritiation of the cannabinoid antagonist SR141716A. J. Chem. Soc., Chem. Commun. 15:1549–1550, 1995.

Seltzman, H. H., Fleming, D. M., Thomas, B. F., Gilliam, A. F., MaCallion, D. S., Pertwee, R. G., Compton, D. R. and Martin, B. R.: Synthesis and pharmacological comparison of dimethylheptyl and pentyl anandamide analogs. Submitted to J. Med. Chem. May 2, 1997.

Sezer, O., Hanci, N., and Anac, O.: Diazoaldehyde Chemistry. part 2. Transdiazotization of beta, gamma– and beta, delta–dioxoaldehydes. Bull. Soc. Chim. Belg. 105(5):223–226, 1996.

Shire, D., Calandra, B., Delpech, M., Dumont, X., Kaghad, M., Le Fur, G., Caput, D., and Ferrara, P.: Structural features of the central cannabinoid CB1 receptor involved in the binding of the specific CB1 antagonist SR 141716A. J. Biol. Chem. 271:6941–6946, 1996.

Showalter, V. M., Compton, D. R., Martin, B. R. and Abood, M. E.: Evaluation of binding in a transfected cell line expressing a peripheral cannabinoid receptor (CB2): Identification of cannabinoid receptor subtype selective ligands. J. Pharmacol. Exp. Ther. 278:989–999, 1996.

Sim, L., J., Selley, D. E., Xiao, Rand Childers, S. R.: Differences in G–protein activation by .mu.– and .sigma.–opioid, and cannabinoid, receptors in rat striatum. Eur. J. Pharmacol. 307:97–105. 1996.

Skaper, S. D., Buriani, A., Dal Toso, R., Petrelli, L., Romanello, S., Facci, L. and Leon, A.: The ALIAmide palmitoylethanolamide and cannabinoids, but not anandamide, are protective in a delayed postglutamate paradigm of excitotoxic death in cerebellar granule neurons. Proc. Natl. Acad. Sci. USA. 93:3984–3989, 1996.

Smith P. B. and Martin B. R.: Spinal mechanisms of .DELTA..sup.9–THC–induced analgesia. Brain Res. 578:8–12, 1992.

Smith, P. B., Compton, D. R., Welch, S. P., Razdan, R. K., Mechoulam, R. and Martin, B. R.: The pharmacological activity of anandamide, a putative endogenous cannabinoid, in mice. J. Pharmacol. Exp. Ther. 270:219–227, 1994.

Snieckus, V.: Directed ortho metalation. Tertiary amide and O–carbamate directors in synthetic strategies for polysubstituted aromatis. Chem. Rev. 90:879–993, 1990.

Sonawane, H.R., Bellur, N. S. Kulkarini, D. G., and Ayyangar, N. R.: Photochemical rearrangement of alpha–chloropropiophenones to alpha–arylpropanoic acids: Studies on chirality transfer and synthesis of (S)–(+)–ibuprofen and (S)–(+)–ketoprofen. Tetrahedron 50(4):1243–1260, 1994.

Song, Z. H. and Bonner, T. I.: A lysine residue of the cannabinoid receptor is critical for receptor recognition by several agonist but not WIN 55212–2. Mol. Pharmacol. 49:891–6, 1996.

Terranova, J.P., Michaud, J. C., Le Fur, G. and Soubrie, P.: Inhibition of long–term potentiation in rat hippocampal slices by anandamide and WIN 55212–2: reversal by SR141716 A, selective antagonist of CB1 cannabinoid receptors. Naunyn Schmiedebergs Arch. Pharmacol. 352:576–9, 1995.

Terranova, J.–P., Storme, J.–J., Lafon, N., Perio, A., Rinaldi–Carmoni, M., Le Fur, G. and Soubrie, P.: Improvement of memory in rodents by the selective cannabinoid receptor antagonist, SR 14176A. Psychopharm. 126:165–172, 1996.

Thomas, B. F., Wei, X. and Martin, B. R.: Characterization and autoradiographic localization of the cannabinoid binding site in rat brain using [3H] 11–OH–.DELTA..sup.9–THC–DMH. J. Pharmacol. Exp. Ther. 263:1383–1390, 1992.

Thomas, B. R., Compton, D. R., Martin, B. R. and Semus, S. F.: Modeling the cannabinoid receptor: a three–dimensional quantitative structure–activity analysis. Mol. Pharm. 40:656–665, 1991.

Thomas, B. F., Mascarella, S. W., Martin, B. R. and Razdan, R. K.: Structure–activity analysis of anandamide analogs: relationship to a cannabinoid pharmacophore. J. Med. Chem. 39:471–479, 1996.

Thomas, B. F., Gilliam, S. F., Burch, D. A., Roche, M. J. and Seltzman, H. H. Comparative receptor binding analyses of cannabinoid agonists and antagonists: further evidence for neuronal cannabinoid receptor subtypes. J. Phar. Exp. Ther., 285 (1): 285–292, 1998.

Tius, M. A., Hill, W. A. G., Zou, X. L., Busch–Petersen, J., Kawakami, J. K., Fernandez–Garcia, M. C., Drake, D. J., Abadji, V., and Makriyannis, A.: Classical/non–classical cannabinoid hybrids. Life Sci., 56(23/24):2007–12, 1995.

Tsou, K., Patrick, S. L. and Walker, J. M.: Physical withdrawal in rats tolerant to .DELTA..sup.9–THC precipitated by a cannabinoid receptor antagonits. Eur. J. Pharmacol. 280:R13–R15, 1995.

Wakefield, B. J.: Organolithium methods, best synthetic methods. Academic Academic Press, Publ. San Diego, Ch. 3, 1988.

Weinstock, L. M., Currie, R. B., and Lovell, A. V.: A general one–step synthesis of alpha–keto esters. Synth. Commun. 11(12):943–946, 1981.

Westlake, T. M., Howlett, A. C. Bonner, T. I., Matsuda, L. A. and Herkenham, M.: Cannabinoid receptor binding and messenger RNA expression in human brain: an in vitro receptor autoradiography and in situ hybridizaqtion histochemistry study of normal aged and Alzheimer's brains. Neuroscience 63:637–52, 1994.

Wiley, J. L., Lowe, J. A., Balster, R. L. and Martin, B. R.: Antagonism of the discriminative stimulus effects of .quadrature..sup.9–THC in rats and rhesus monkeys. J. Pharmacol. Exp. Ther. 275:1–6. 1995.

Zhang, C. Moran, E. J., Woiwode, T. F., Short, K. M., and Mjalli, A. M. M.: Synthesis of Tetrasubstituted Inidazoles via alpha–(N–acyl–N–alkylamino)–beta–ketoamides on Wang Resin. Tetrahedron Lett. 37:751–754, 1996.

Barth, F., Rinaldi–Carmona, M., Millan, J., Derocq, J.–M., Bouaboula, M., Casellas, P., Congy, C., Oustric, D., Sarran, M., Calandra, B., Portier, M., Shire, D., Brelire, J. C. and Le Fur, G.: SR 144528, a potent and selective antagonist of the CB2 receptor. International Cannabis Research Society abstract, to be presented Jun., 1997.

Bradford, M. M.: A rapid and sensitive method for the quantiation of microgram quantities of protein utilizing the principle of protein–dye binding. Anal. Biochem. 72:248–254, 1976.

Campaigne, E. and Archer, W. L.: in Org. Synth. (Eds.), vol. II, pp. 331 1963.

Casellas, P., Monsif, Bouaboula, M., Calandra, B., Canat, X., Carayon, P., Derocq, J.–M., Dussossoy, D., Galiegue, S., Marchand, J., Poinot–Chazel, C., Rinaldi–Carmona, M., Shire, D. and Le Fur, G.: Study of the distribution of peripheral cannabinoid receptor (CB2) and of the signaling pathway associated with CB2 stimulation. International Cannabis Research Society abstract, 1996.

Devane, W. A., Hanus, L., Breuer, A., Pertwee, R. G., Stevenson, L. A., Griffin, G., Gibson, D., Mandelbaum, A., Eager, A. and Mechoulam, R.: Isolation and structure of a brain constituent that binds to the cannabinoid receptor [see comments]. Science 258:1946–1949, 1992a.

Cheng, Y.–C. and Prusoff, W. H.: Relationship between the inhibition constant (Ki) and the concentration of inhibitor which causes 50 percent inhibition (I50) on an enzymatic reaction. Biochem. Pharmacol. 22:3099–3108, 1973.

Mechoulam, R., Ban–Shabat, S., Hanus, L., Ligumsky, M., Kaminski, N. E. Schatz, A. R., Gopher, A., Almog, S., Martin, B. R., Compton, D. R. et al.: Identification of an endogenous 2–monoglyceride, present in canine gut, that binds to cannabinoid receptors. Biochem. Pharmacol. 50:83–90, 1995.

* cited by examiner

COMPOUNDS HAVING UNIQUE CB1 RECEPTOR BINDING SELECTIVITY AND METHODS FOR THEIR PRODUCTION AND USE

BACKGROUND OF THE INVENTION

1. Field of Invention

The present invention relates to compounds that are analogs of SR141716A having unique CB1 receptor interactions and pharmacological profiles and their use in treatment of a variety of disorders such as substance abuse, obesity, schizophrenia, and memory dysfunction.

2. Discussion of the Background

The use of *Cannabis sativa, Cannabis indica*, and cannabinoid preparations in medicinal, religious, industrial, and social settings has an extensive history, with the first recorded medicinal use occurring in 2737 B.C. Despite its recognition and use as a medicinal natural product by many cultures, including that of the aboriginal in the United States, its use in western medicine began to decrease early in this century. With the passing of the Marijuana Tax Act of 1937, its cultivation and use were effectively prohibited in the U.S. In 1942, the U.S. Pharmacopeia removed marijuana from its listing. Despite marijuana usage falling into disfavor during this time, the medicinal properties of cannabis continued to be investigated. These studies were directed toward both therapeutic applications and the understanding of the mechanism(s) of action. As a result, the primary psychoactive constituent $\Delta^9$-tetrahydrocannabinol (THC) was identified, and the structure-activity relationships (SARs) of the cannabinoids were explored (Mechoulam et al., 1970). These studies ultimately resulted in the classification of the cellular effects of a wide variety of cannabinoids in cellular and laboratory animal test systems (Martin, 1986). SARs were generated in man and laboratory animals, particularly with regard to psychotomimetic and analgesic activity (Razdan et al., 1986). Although some studies have shown therapeutic utility in the treatment of cancer chemotherapy nausea, glaucoma, and other disorders, the only therapeutic application for cannabis or cannabinoids with FDA approval is the use of Marinol® ($\Delta^9$-THC in sesame oil) as an anti-emetic.

The continued synthesis and identification of novel cannabinoids, particularly within the last 20 years, has provided researchers with a variety of chemical probes that have facilitated a rapid expansion in the knowledge of the neurochemical substrates and mechanisms of action of cannabis and cannabinoids. The discovery of the nonclassical cannabinoids (Johnson and Melvin, 1986) and the use of the bicyclic cannabinoid [$^3$H]CP55,940 as a high affinity ligand enabled the identification, localization and molecular characterization of cannabinoid receptors (Devane et al., 1988; Herkenham et al., 1990; Matsuda et al., 1990) and did much to initiate and sustain this renewed interest in cannabinoid research. Indeed, the discovery of other classes of cannabimimetic compounds such as the aminoalkylindole (WIN55212-2) and, more recently, the endogenous cannabinoid anandamide (arachidonylethanolamide; Devane et al., 1992a), were in some ways dependent upon the discovery of [$^3$H]CP55,940. These compounds and others have resulted in the discovery of additional cannabinoid receptors, with the predominant form in the central nervous system (CNS) designated the CB1 site and the form found primarily in the periphery denoted the CB2 site (Munro et al., 1993). Similarly, the identification of the CB2 receptor has fostered the synthesis and characterization of receptor-selective cannabinoid ligands, such as 1-deoxy-11-hydroxy-$\Delta^8$-THC-DMH (Huffmann et al., 1996). All of the varied structural classes of cannabinoid ligands have been examined for their selectivity at CB1 and CB2 receptor systems (Showalter et al., 1996; Felder et al., 1995) and their influence on the second messenger systems coupled to these receptor subtypes (Howlett et al., 1988; Bayewitch et al., 1995) and the endogenous neurochemicals and enzymes (Deutsch and Chin, 1993; Childers and Deadwyler, 1996) involved in cannabinoid activity. In addition to providing high affinity ligands and novel tools for examining cannabinoid mechanisms, these compounds have also provided new templates for drug discovery.

More recently, Rinaldi-Carmona et al. (1994) reported SR141716A (having the structure of Formula (I)), a potent cannabinoid antagonist with nanomolar affinity that represents a unique chemical tool for further characterizing the cannabinoid receptor system in the CNS.

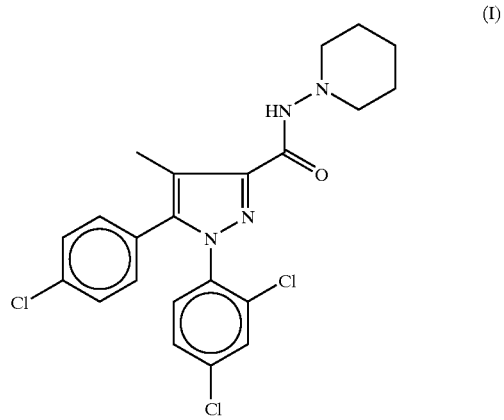

That is, prior to the discovery of SR141716A, the identification of an antagonist for the cannabinoid receptor remained one of the final undiscovered pharmacological tools for further elucidating the mechanism of action and pharmacological relevance of cannabis and cannabinoids. While some compounds, such as cannabidiol or $\Delta^{9,11}$-THC (Beardsley et al., 1987), had previously been reported to have antagonist activity, their potencies were extremely low. More recently, other compounds were purported to be cannabinoid antagonists, such as WIN56098, WIN54461 (Eissenstat et al., 1995) and AM630 (Pertwee et al., 1995a); however, these molecules are also less potent than SR141716A and, in the case of WIN56098, have not been convincingly shown to be antagonists (Pacheco et al., 1994). SR141716A was the first compound reported to be both an antagonist in vitro and sufficiently potent in vivo to produce a withdrawal syndrome in cannabinoid tolerant animals (Aceto et al., 1995; Tsou et al., 1995). SR141716A has also been demonstrated to have therapeutic potential in treating obesity, both in laboratory animal studies (DiMarzo et al., 2001), and in human obese males (Le Fur et al., 2001). Furthermore, SR141716A blocked acute psychological and physiological effects of smoked marijuana without altering THC pharmacokinetics (Heustis et al., 2001). Therefore, cannabinoid antagonists constitute an additional family of cannabinoid receptor ligands that are currently being considered as rational compounds for pharmacotherapeutics and structure-activity relationship analyses. It is of interest to us and other cannabinoid researchers to determine whether these compounds interact within the same recognition site on the cannabinoid receptor and whether the population of neuronal receptor sites to which SR141716A binds is the same as that with which classical and nonclassical cannabinoids interact.

Receptor-Binding Properties of SR141716A

It is generally accepted that there are two types of cannabinoid receptors: CB1 and CB2. CB1 receptors are primarily expressed in the CNS and to a lesser extent in selected tissues of the periphery; CB2 receptors have been suggested to be limited to peripheral tissues. [3H] SR141716A in vitro has high affinity for CB1 (Rinaldi-Carmoni et al., 1994; Rinaldi-Carmoni et al., 1995a; Petitet et al., 1996; Hirst et al., 1996; Thomas et al., 1997) and binds to CNS receptor populations with the same pattern of distribution (Rinaldi-Carmona et al., 1995b) as that observed with CP55,940 (Herkenham et al., 1990), 11-OH-$\Delta^9$-THC-DMH (Thomas et al., 1992) and WIN55212-2 (Jansen et al., 1992; Kuster et al., 1993). This similarity of distribution provides further evidence that SR141716A binds specifically to neuronal cannabinoid receptors. SR141716A has marked selectivity for the CB1 over the CB2 receptor: the $K_i$ for CB1 is over 50-fold lower (Rinaldi-Carmona et al., 1994; Felder et al.; 1995; Showalter et al., 1996). This degree of selectivity is relatively unparalleled among cannabinoid compounds. WIN55212-2, by comparison, has approximately 20-fold (Felder et al., 1995) or 7-fold (Showalter et al., 1996) greater selectivity for CB2, while CP55,940 has approximately equal affinity at these two receptor sites.

It is important to emphasize that the nature and locus of interaction of any cannabinoid ligand with the cannabinoid receptor is unknown. Receptor mutation studies using chimeras created between CB1 and CB2 receptor sequences have shown that alterations in the extracellular loop region between helices three and four of the seven transmembrane regions differentially affect the binding of SR141716A and CP-55,940, leading Shire et al. (1996) to conclude that the binding of these two compounds most likely involves different amino acids, if not different regions of the receptor. However, as the authors point out, modest changes in the three-dimensional conformation of receptors brought about by amino-acid substitutions in regions other than those involved in ligand recognition can alter the selectivity of a receptor (Fong et al., 1994). Therefore, there could be an overlapping receptor region that is capable of interacting with the antagonist SR141716A and cannabinoid agonists. Indeed, many antagonists share some but not all of the binding domain of the agonists, an idea supported by the observation that antagonists are frequently larger than agonists (Kenakin, 1993).

In-Vitro Effects of SR141716A on Signal Transduction Systems

SR141716A blocks cannabinoid-induced (CB1-coupled) inhibition of adenylate cyclase (Rinaldi-Carmona et al., 1994; Hirst et al., 1996), the predominate signal transduction mechanism of cannabinoids in the CNS. Because of its low affinity for the CB2 receptor, it is a poor antagonist of the CB2 receptor mediated inhibition of cAMP accumulation (Felder et al., 1995). The effects of SR141716A on cannabinoid-mediated modulation of potassium and calcium channels have not received as much study as the adenylate cyclase system. However, anandamide directly inhibits Shaker-related potassium channels that are found ubiquitously in the mammalian brain, as does $\Delta^9$-THC, and the inhibition occurs through a pertussis toxin-insensitive mechanism and is not prevented by SR141716A (Poling et al., 1996). In tissue preparations, SR141716A reverses cannabinoid-mediated inhibition of long-term potentiation in rat hippocampal slices (Terranova et al., 1995), contractions of mouse vas deferens (Rinaldi-Carmona, et al., 1994), electrically evoked contractions of the guinea-pig myenteric plexus-longitudinal muscle preparation (Pertwee et al., 1996a) and electrically invoked contractions of mouse urinary bladder (Pertwee et al., 1996b).

In-Vivo Effects of SR141716A

SR141716A blocks several of the primary pharmacological effects of cannabinoid agonists in laboratory animals. Pretreatment of mice with SR141716A prevents cannabinoid agonists from producing hypothermia, catalepsy, analgesia and decreased locomotor activity—the "mouse tetrad" of cannabinoid effects (Compton et al., 1996). SR141716A antagonizes $\Delta^9$-THC's discriminative stimulus properties in pigeons (Mansbach et al., 1996), rats, and rhesus monkeys (Wiley et al., 1995). Perhaps even more indicative of the potency of this antagonist is its ability in the 1–10 mg/kg range, to precipitate a withdrawal syndrome characterized by disorganized patterns of sequences of motor behavior in rats chronically treated with THC (Aceto et al., 1995; Tsou et al., 1995). These results have led some go investigators to suggest that because the psychotomimetic effects of cannabinoids can be blocked in laboratory animals, SR141716A should be capable of blocking, and perhaps reversing, cannabis intoxication in man. In addition to SR141716A, various analogs of SR141716A have been synthesized and shown to antagonize the in vitro effects of cannabinoid agonists and to bind to the same regions in the CNS (Gatley et al., 1996; Thomas et al., 1998; Rinaldi-Carmona et al., 1998), or in some instances act as partial agonists in certain cannabinoid assays (Houston et al., 1997).

Therapeutic Potential of Cannabinoid Antagonists

The potential therapeutic activities of SR141716A are in some ways dependent on the distribution of CB1 cannabinoid receptors in the CNS, the regions to which the receptor-invested neurons project, or to the cell-line that is being affected. For example, CB, receptors are localized in regions of the hippocampus, which would indicate that modulation of the cannabinoid system might alter the processing and storage of information (Herkenham et al., 1990). The globus pallidus and the substantia nigra pars reticulata are also heavily invested with cannabinoid receptors localized on the axon terminals of striatal efferent neurons, which suggests that alteration of this system might affect movement control. Cannabinoids are known to produce a number of cellular effects (Martin, 1986), and cannabinoid agonists exhibit a wide range of pharmacological activities in laboratory animals and man (Dewey, 1986). Because of the diversity of these effects, the therapeutic utility of cannabinoid antagonists could be quite wide-ranging. Indeed, it has recently been shown that anandamide levels in mouse uterus are associated with uterine receptivity for embryo implantation (Schmid et al., 1997). Furthermore, anandamide levels in the preimplantation mouse uterus are at the highest level yet determined in any mammalian tissue. Since anandamide and CP-55,940 both inhibit implantation, and this effect is reversed by SR141716A, cannabinoid antagonists could play a role in the treatment of early pregnancy failures or female infertility. Even dopamine release in guinea pig retina is inhibited by activation of cannabinoid receptors that appear to be tonically regulated by an endogenous ligand or are pre-coupled to the G-protein effector system (Schlicker et al., 1996). Thus, the relatively recent discovery of cannabinoid antagonists has led to the rapid identification and expansion of systems under cannabinergic control which represent potential therapeutic indications for cannabinoid modulation.

The antagonist activity of SR141716A in the CNS has led to speculation that this compound may be able to prevent or reverse cannabis intoxication in man. This activity could be useful in drug abuse intervention. For example, a depot form might prevent drug-seeking and relapse. The utility of SR141716A in understanding and treating drug abuse might extend beyond direct antagonism. An antagonist used as a probe could elucidate the biochemical basis of cannabis abuse, and substance abuse in general, and thus be useful in developing other substance abuse treatment modalities. Evidence in support of this contention can be summarized as follows: Cannabinoid receptors do not reside on mesencephalic dopaminergic neurons projecting to either the caudate-putamen or the nucleus accumbens (Herkenham, 1992). However, cannabinoid receptors are located in these regions, and cannabinoids elevate extracellular dopamine levels there (Ng Cheong Ton et al., 1988; Chen et al., 1990) and in other regions possessing cannabinoid receptors (Chen et al., 1993). Because drugs that elevate dopamine levels in the striatum, such as cocaine, have abuse liability in humans (Kornetsky, 1985), SR141716A might be expected to attenuate the abuse liability of cannabinoids and other abused substances through its ability to diminish their stimulation of dopaminergic activity in the brain's reward circuitry. However, in behavioral studies of reward and aversion (Sanudo-Pena et al., 1997), cannabinoid agonists induced place aversion while cannabinoid antagonists induced place preference, a finding opposite to what one might anticipate based on the effects of these compounds on the striatal dopamine system. In rats, the concurrent administration of SR141716A during a 30-day chronic ethanol exposure increases the preference for ethanol; whereas the administration of the CB1 antagonist after chronic alcohol or at the time of withdrawal drastically diminishes the ethanol preference (Lallemand et al., 2001). Finally, in CB1 knock-out mice that do not respond to cannabimimetic agents, the acute effects of opiates are unaffected, but the reinforcing properties of morphine and the severity of the withdrawal syndrome are strongly reduced (Ledent et al., 1999). The diminution of opioid withdrawal in CB1 cannabinoid receptor knockout mice supports the notion that the cannabinoid system modulates dependence and withdrawal. Also consistent with the notion that cannabinoid agents can modulate withdrawal is the observation that SR 141716A administered repeatedly to morphine-dependent rats lessened the intensity of naloxone-precipitated withdrawal (Rubino et al., 2000).

SR141716A analogs might also have medicinal properties through their ability to modulate the cannabinoid system in the absence of a pre-existing effect produced by an exogenous compound such as $\Delta^9$-THC. In this instance, additional utility or medicinal potential for cannabinoid antagonists depends upon their ability to antagonize the effects of endogenous ligands, such as anandamide, which are contributing to a cannabinergic tone. Alternatively, constituitive coupling of cannabinoid receptors to G-proteins provides therapeutic potential for inverse agonists. Perhaps the most convincing demonstration of the therapeutic utility of cannabinoid antagonists or inverse agonists in the absence of exogenous agents was demonstrated in the report by Le Fur et al. (2001). In these studies, treatment of obese males with SR141716A resulted in a significant decrease in body weight that continued over the entire period of treatment. This was an obvious, albeit until then unproved, reversal of the ability of cannabinoid agonists, including endogenous agonists, to increase appetite. However, the therapeutic utility of cannabinoid antagonists has yet to be fully explored, and experimental studies of SR141716A and its effects on cannabinoid systems exhibiting tone continue to identify promising pharmacological activities (Collins et al., 1995; Lichtman et al., 1995; Lichtman and Martin, 1996, Terranova et al., 1996; Richardson et al., 1997; Smith and Martin, 1992; Smith et al., 1994; Compton et al., 1996; Pertwee and Fernando, 1996b). Thus, the discovery of cannabinoid antagonists has led to the rapid identification and expansion of systems under cannabinergic control which represent potential therapeutic indications for cannabinoid modulation.

Accordingly, there is a need to identify cannabinoid antagonists with increased CB1 selectivity, relative to SR141716A, to better target treatment regimens. It is also possible that compounds can be identified that selectively displace the various structural classes of cannabinoid ligands at the CB1 receptor. For example, a compound might fully displace [$^3$H]CP55940 and [$^3$H]SR141716A with reasonable affinity, while simultaneously much less able, or unable, to displace [$^3$H]WIN55212-2 from the CB1 receptor in humans (hereafter referred to as "WIN-sparing"). These compounds might be anticipated to possess unique pharmacological properties, particularly since it is unclear whether the eicosanoids, anandamide, 2-arachidonylglycerol and 2-arachidonylglyceryl ether are the only, or even the primary, endogenous ligands, and it remains to be determined how these eicosanoid compounds interact with the CB1 receptor.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

SUMMARY OF THE INVENTION

Figure 1A:
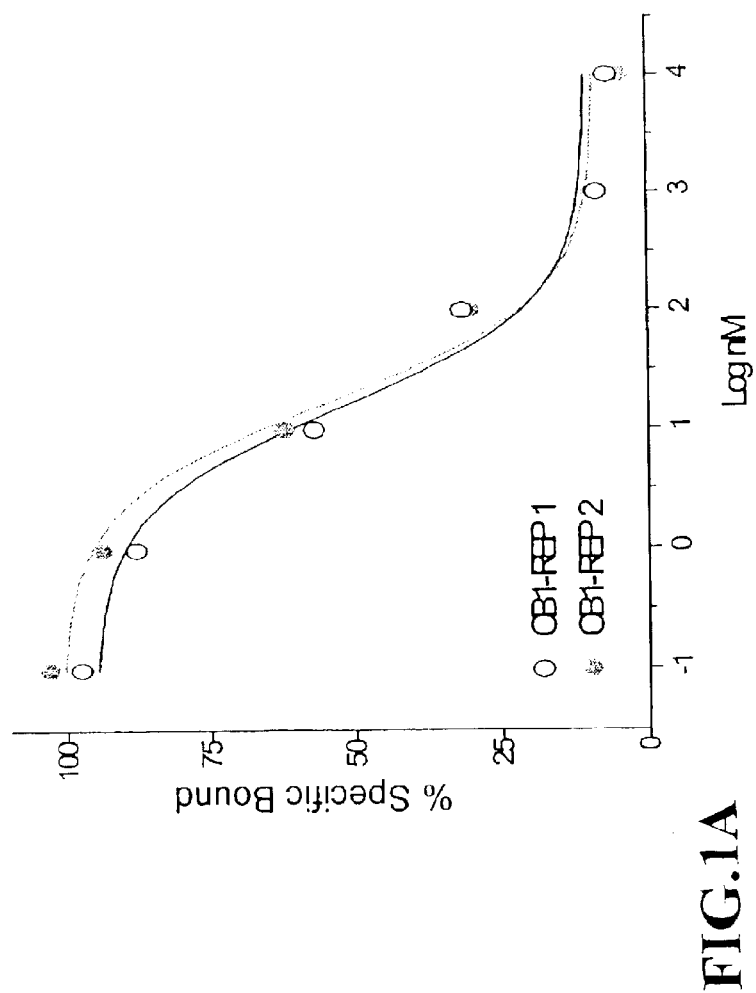
FIGS. 1A–C provide displacement curves for SR141716A against [$^3$H]CP55,940 (A), [$^3$H]SR141716A (B) and [$^3$H]WIN55212-2 (C) in hCB1 receptor transfected cells. The Ki values, the standard error of the mean (SEM) of the Ki values, and the percent maximum displacement observed (% Disp.) are provided in the inset.

Accordingly, one object of the present invention is to provide a cannabinoid antagonist that has high CB1 selectivity.

A further object of the present invention is to provide a cannabinoid antagonist that has a combination of high CB1 selectivity, while providing WIN-sparing properties.

A further object of the present invention is to provide a pharmaceutical composition containing the cannibinoid antagonist of the present invention and a pharmacologically acceptable carrier.

A further object of the present invention is to provide a method for the treatment of CB1 receptor related disorders.

These and further objects of the present invention have been satisfied by the discovery of a compound comprising:

an alkyl amide of formula (II) or formula (III)

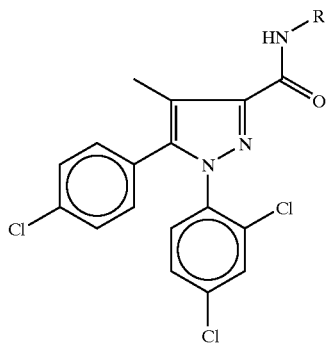

(II)

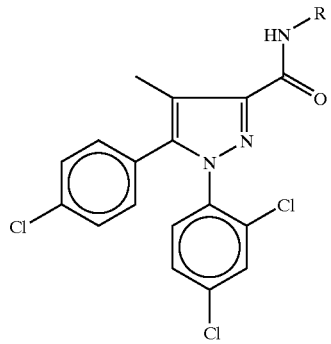

(II)

where R is a linear or branched hydrocarbon group having from 7 to 12 carbon atoms, preferably from 7 to 9 carbons, most preferably linear hydrocarbon groups of 7 to 9 carbon atoms. The present invention further relates to ring-constrained compounds having a structure of Formula III,:

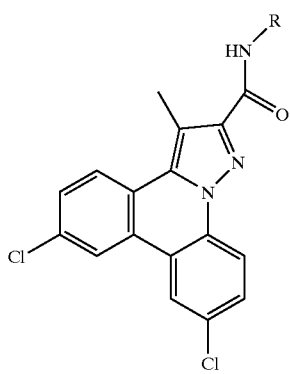

(III)

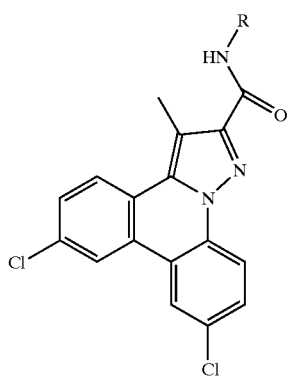

(III)

wherein R is as described above, or R can be N-piperidinyl.

The present compounds interact with the human CB1 receptor, and displace both a CB1 agonist (CP-55,940) and an antagonist (SR141716A), but are unable to effectively displace the prototypical CB1 agonist WIN55212-2. Furthermore, the compounds possess inverse agonist activity (indicating that they bind to cannabinoid receptors and modulate cannabinoid tone), while being unable to antagonize the effects of the prototypical aminoalkylindole cannabinoid agonist WIN55212-2. Thus, the compounds of the present invention display a unique selectivity in displacing the various standard radioligands used from the CB1 receptor. Prior to the present invention, compounds within structural classes that bind to the CB1 receptor (i.e., the aminoalkylindole agonists such as WIN55212-2, the bicyclic cannabinoids such as CP55,940 and the pyrazole inverse agonists such as SR141716A) had always been shown to displace each other in a competitive fashion.

There are several possibilities for the nature of SR141716A binding: 1) binding at a distant yet interacting site from agonists on the cannabinoid receptor; 2) binding at the site also occupied by agonists, but in a manner unlike that previously characterized for agonists; 3) binding at a site occupied by, and in a manner consistent with, agonists. Thus, it is of interest to note that SR141716A can fully displace [$^3$H]SR141716A, [$^3$H]CP55,940 and [$^3$H]WIN55212-2, and shows reasonably high affinity for the wherein R is a linear or branched hydrocarbon group having from 7 to 12 carbons, or in the case of Formula III, R can be N-piperidinyl, pharmaceutical compositions having such compounds therein, and uses of such compounds in the treatment of CB1 receptor related disorders.

DETAILED DESCRIPTION OF THE INVENTION

Figure 1B:
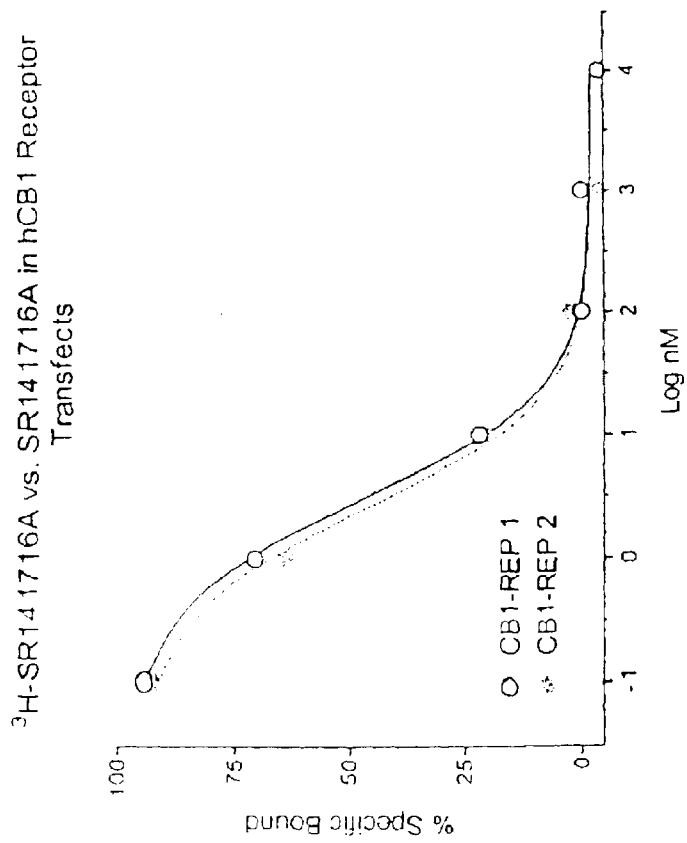
Figure 1C:
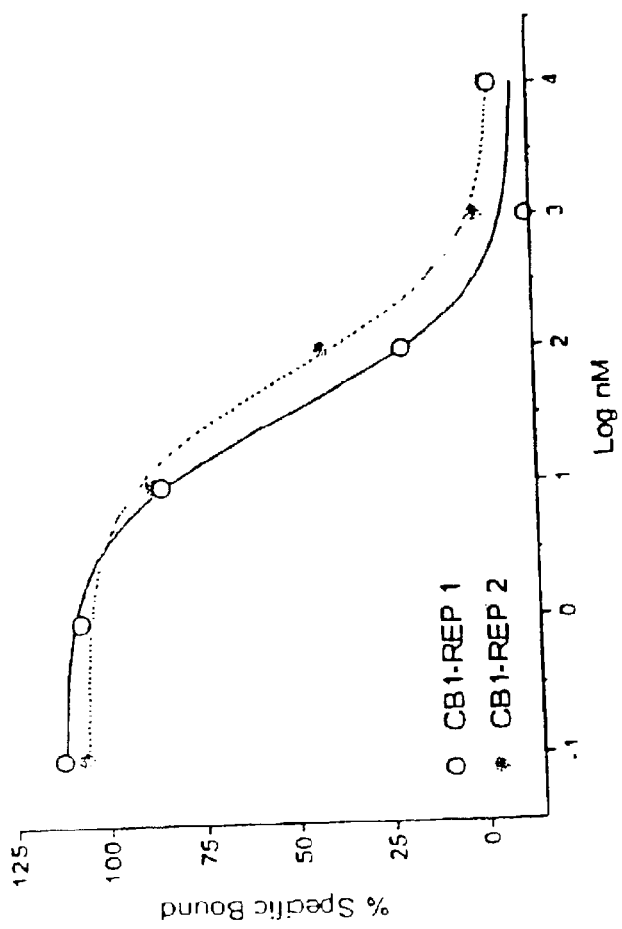

The present invention relates to compounds that act as cannabinoid antagonists with high selectivity for the CB1 receptor, while providing WIN-sparing properties. The compounds of the present invention have the general formula (II):

CB1 receptor when measured by each radioligand (FIGS. 1A–C). Generally, ligands from each structural class of cannabimimetic compounds that possess affinity for the CB1 receptor have always been shown to fully displace ligands across all other structural classes of cannabimimetic compounds that bind to the CB1 receptor. While this does not preclude the possibility that SR141716A binds at the site occupied by, and in a similar manner to, the agonists CP55,940 and WIN55212-2, it suggests that the antagonist analogs of the present invention interact with unique binding sites, or in unique ways at the same binding site.

In fact, when the R group is less than 6 carbons (i.e. methyl, ethyl, propyl . . . pentyl), the compounds do not show this selectivity in either rat or human brain preparations, effectively acting as one would expect from prior reports, namely, displacement of the WIN, CP55,940 and SR141716A compounds competitively. The present compounds, on the other hand, show this selectivity in human CB1 receptor transfected cell lines and human brain membrane preparations (both cortex and cerebellum), but do not readily show the selectivity in rat brain membrane preparations.

Despite a very high degree of sequence homology between rat and human CB1 receptors, the alkyl amides of the present invention beyond C6 interact at rat and human CB1 receptors quite differently. The pharmacological activity of these compounds in a mouse vas deferens assay demonstrated that these compounds also differed dramatically in their ability to antagonize the effects of WIN55212-2, as compared to the prototype compound SR141716A.

This unique pharmacological profile for the present compounds makes them useful for treatment of a variety of conditions that depend on activity/selectivity at the CB1 receptor, and particularly on the ability to discriminate between WIN, CP55,940 and SR141716A agonists/inverse agonists. Such conditions include, but are not limited to, obesity, schizophrenia and memory dysfunction. Additionally, due to the structural similarities between the CP55,940 agonist and THC, it is possible that the present compounds can be used to block the effects of smoked marijuana, while not blocking the binding of endogenous compounds.

The compounds of the present invention can be prepared by any desired synthetic method. Exemplary of such methods is the method shown below for preparation of SR141716A, which can be easily modified by proper selection of the alkyl amine in the last step of the synthesis (in place of the cyclohexyl hydrazine used to prepare SR141716A):

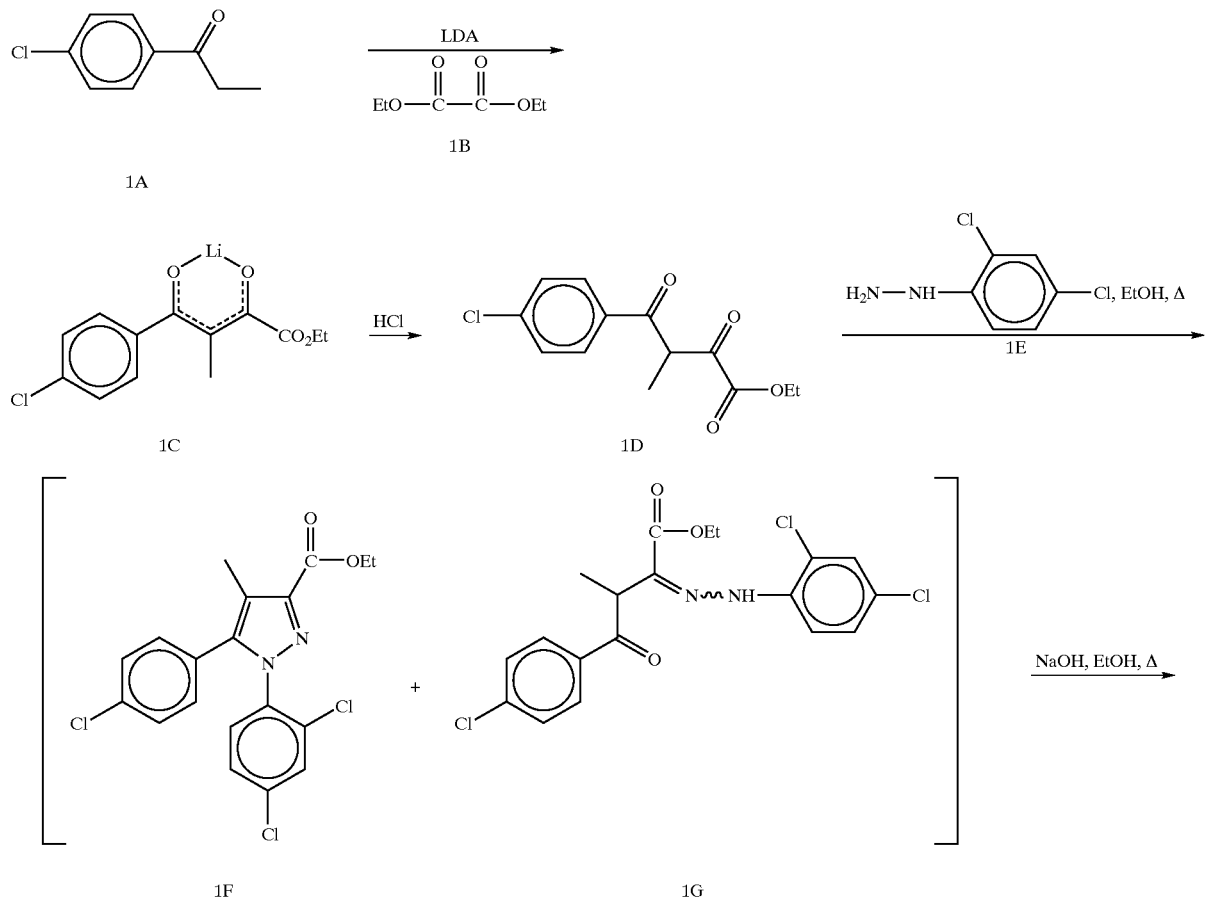

The compounds may be administered in an effective amount by any of the conventional techniques well-established in the medical field. For example, the compounds may be administered orally, intravenously, peritoneally, nasally or intramuscularly. When so administered, the inventive compounds may be combined with any of the well-known pharmaceutical carriers and additives that are customarily used in such pharmaceutical compositions. For a discussion of dosing forms, carriers, additives, pharmacodynamics, etc., see Kirk-Othmer Encyclopedia of Chemical Technology, Fourth Edition, Vol. 18, 1996, pp. 480–590, incorporated herein by reference. The patient is preferably a mammal, with human patients especially preferred. Effective amounts are readily determined by those of ordinary skill in the art. The present compounds have little or no toxicity or lethality at amounts up to 30 mg/kg in mice.

The compounds of the present invention can be administered as a single dosage per day, or as multiple dosages per day. When administered as multiple dosages, the dosages can be equal doses or doses of varying amount, based upon the time between the doses (i.e. when there will be a longer time between doses, such as overnight while sleeping, the dose administered will be higher to allow the compound to be present in the bloodstream of the patient for the longer period of time at effective levels). Preferably, the compound and compositions containing the compound are administered as a single dose or from 2–4 equal doses per day. Preferably the effective dosage is in a range of from 0.01 mg/kg to 900 mg/kg, more preferably from 1 mg/kg to 90 mg/kg.

Suitable compositions containing the present compounds further comprise a physiologically acceptable carrier, such as water or conventional pharmaceutical solid carriers, and if desired, one or more buffers and other excipients.

EXAMPLES

Methods. A series of alkyl amide and hydrazide analogs were synthesized at the 3-position substituent and tested for their ability to displace [$^3$H]CP55,940, [$^3$H]SR141716A, and [$^3$H]WIN55212-2 from a variety of CB1 and CB2 receptor preparations. Over 50 analogs of SR141716A have been synthesized at this position, and tested for receptor affinity in rat brain membrane preparations (rat CB1), human CB2 receptor transfects, human CB1 receptor transfects, and human brain membrane preparations (both cortex and cerebellum). These compounds were also tested for their ability to modify receptor-G-protein coupling using the GTP-γ-[$^{35}$S] assay, and to possess pharmacological activity in an in situ assay of cannabimimetic activity (mouse vas deferens). The synthesis of most of the analogs at the 3-position were carried out in a manner similar to a previously published synthesis of SR141716A (Barth et al., 1995a; Barth et al., 1995b; Barth et al., 1997b; Seltzman et al., 1995; Seltzman, 2001) by condensation of the respective hydrazines and amines with the pyrazole acid chloride (see the sythetic scheme above). A detailed description of the methods used for pharmacological characterization is provided below.

CB1 receptor affinity in rat brain. All of the compounds were tested for their ability to displace [$^3$H]CP55,940 and [$^3$H]SR141716A, and selected compounds were also tested for their ability to displace [$^3$H]WIN55212-2 (Tables 1 and 2).

TABLE 1

Amide Analogs at the 3-Position - Displacement of Various Radioligands in Whole Rat Brain (CB1) Membrane Preparations

| | | $^3$H-CP55940 | | | $^3$H-SR141716A | | | $^3$H-WIN55212-2 | | |
|---|---|---|---|---|---|---|---|---|---|---|
| Compound | Substituted Group | $K_i$ (nM) | SEM | Max. Disp. % | $K_i$ (nM) | SEM | Max. Disp. % | $K_i$ (nM) | SEM | Max. Disp. % |
| SR141716A | | 6.18 | 1.2 | 86.6 | 1.18 | 0.10 | 96.5 | | | |
| SR144528 | | 74.1 | 11.4 | 84.7 | 81.7 | 19.3 | 68.6 | | | |
| MF9725-9D | precursor - diketone | nr | | 26.7 | Nr | | 33.7 | | | |
| SH9631-55 | pyrazole acid (intermediate) | nr | | 8.2 | Nr | | 0 | | | |
| SH-9631-56 | pyrazole ethyl ester (intermediate) | 31.8 | 11.5 | 91.7 | 28.9 | 3.5 | 96.9 | | | |
| MF9725-54C | N-(1-ethyl) | 46.3 | 1.5 | 91.4 | 61.5 | 3.3 | 100 | | | |
| MF9725-55C | N-(1-propyl) | 29.9 | 0.55 | 97.4 | 23.6 | 1.1 | 100 | | | |
| MF9725-64-17 | N-(1-butyl) | 13.4 | 1.0 | 91.9 | 12.8 | 4.5 | 100 | 32.8 | 26.0 | 90.8 |

TABLE 1-continued

Amide Analogs at the 3-Position - Displacement of Various Radioligands in Whole Rat Brain (CB1) Membrane Preparations

| | | ³H-CP55940 | | | ³H-SR141716A | | | ³H-WIN55212-2 | | |
|---|---|---|---|---|---|---|---|---|---|---|
| Compound | Substituted Group | $K_i$ (nM) | SEM | Max. Disp. % | $K_i$ (nM) | SEM | Max. Disp. % | $K_i$ (nM) | SEM | Max. Disp. % |
| MF9725-67-17 | N-(1-pentyl) | 11.4 | 0.49 | 91.4 | 6.83 | 1.2 | 100 | 12.6 | 4.5 | 94.4 |
| MF9725-132-25 | N-(1-hexyl) | 18.2 | 3.9 | 87.3 | 10.7 | 0.62 | 98.6 | 16.6 | 4.4 | 77.9 |
| MF9725-133-25 | N-(1-heptyl) | 46.2 | 13.9 | 81.7 | 19.0 | 1.2 | 97.9 | 28.8 | 2.8 | 69.6 |
| MF10110-119-11 | N-[1-(1,1-dimethlheptyl)] | 181 | 5.8 | 83.2 | 21.6 | 3.3 | 76.4 | 10.4 | 3.3 | 72.2 |
| MF9879-164-28 | N-(1-octyl) | 135 | 16.7 | 80.2 | 37.4 | 6.0 | 75.2 | 36.2 | 2.7 | 68.4 |
| MF10110-10-21 | N-(1-nonyl) | 333 | 128 | 79.5 | 88.2 | 5.5 | 85.8 | 68.2 | 4.7 | 68.6 |
| MF9725-68-10 | N-(2-methylpropyl) | 11.5 | 0.16 | 96.7 | 9.22 | 0.17 | 100 | 46.4 | 4.0 | 90.9 |
| MF9725-65-11 | N-(2-propyl) | 29.4 | 0.76 | 88.3 | 12.9 | 4.7 | 100 | 36.1 | 14.7 | 90.6 |
| MF9725-131-25 | N-hydroxy | 1686 | 481 | 58.4 | 1564 | 625 | 65.7 | | | |
| MF9725-93-31 | N-(2-OH-ethyl) | 385 | 13.0 | 73.2 | 343 | 7.8 | 85.5 | | | |
| MF9725-94-31 | N-(3-OH-propyl) | 160 | 19.4 | 86.6 | 156 | 2.5 | 100 | | | |
| MF9725-95-31 | N-(4-OH-butyl) | 154 | 2.2 | 88.7 | 143 | 12.3 | 97.6 | | | |
| MF9725-105-38 | (+)-N-(2-OH-1-methylethyl) | 117 | 0.25 | 88.1 | 123 | 2.1 | 96.8 | | | |
| MF9725-106-39 | (−)-N-(2-OH-1-methylethyl) | 117 | 27.7 | 89.7 | 99.8 | 3.9 | 100 | | | |
| MF9725-33D | N-morpholin-4-yl | 22.9 | 2.2 | 96.2 | 21.0 | 2.2 | 100 | | | |
| MF9725-66-11 | N-(1-cyclohexyl) | 2.46 | 0.10 | 96.1 | 1.07 | 0.13 | 100 | 2.23 | 0.15 | 92.6 | nr = no displacement at concentrations tested

TABLE 2

Hydrazide Analogs at the 3-Position - Displacement of Various Radioligands in Whole Rat Brain (CB1) Membrane Preparations

| | | ³H-CP55940 | | | ³H-SR141716A | | | ³H-WIN55212-2 | | |
|---|---|---|---|---|---|---|---|---|---|---|
| Compound | Substituted Group | $K_i$ (nM) | SEM | Max. Disp. % | $K_i$ (nM) | SEM | Max. Disp. % | $K_i$ (nM) | SEM | Max. Disp. % |
| SR141716A | | 6.18 | 1.2 | 86.6 | 1.18 | 0.10 | 96.5 | | | |
| SR144528 | | 74.1 | 11.4 | 84.7 | 81.7 | 19.3 | 68.6 | | | |
| MF9879-34-8 | N-hydrazide | 374 | 26.7 | 68.4 | 602 | 57.8 | 85.9 | | | |
| MF9879-47-23 | N-(1-methyl hydrazide) | 555 | 85.7 | 72.9 | 429 | 46.4 | 88.8 | | | |
| MF9879-48-11 | N-(1-ethyl hydrazide) | 143 | 9.5 | 88.1 | 72.0 | 7.6 | 97.1 | | | |
| MF9879-7-6 | N-(1-propyl hydrazide) | 74.8 | 11.5 | 87.8 | 64.0 | 12.1 | 92.9 | | | |
| MF9725-179-32 | N-(1-butyl hydrazide) | 50.9 | 6.4 | 92.1 | 40.6 | 1.5 | 100 | 45.6 | 33.7 | 78.9 |
| MF9725-181-32 | N-(2-methylpropyl hydrazide) | 41.8 | 1.5 | 88.9 | 35.5 | 1.2 | 94.5 | | | |

The CB1 receptor binding data in rat brain for this series of analogs demonstrated that as the size of the carbon chain is increased, modest increases in the binding affinity were observed, up to the C-5 chain. With the C-6 chain, increases in binding affinity were no longer evident. This trend was apparent in the alkylamides, hydroxyalkylamides, and alkylhydrazides. The presence of a chiral center in the compound appeared not to be a factor as there was not a significant difference in the binding affinity to the receptor between the (R)- and (S)-hydroxymethylethyl amides. They both exhibited a 20-fold decrease in binding affinity over SR141716A, as did the rest of the hydroxyalkylamide series. This implies that the presence of the second electronegative heteroatom decreases receptor binding affinity. When a methylene unit in the piperidinyl ring is replaced with an oxygen, as in the morpholino derivative only moderate binding affinity is observed, again implying that the electronegativity of the oxygen decreases receptor binding affinity. Similarly, the replacement of the nitrogen atom in the piperidinyl ring of SR141716A with a methylene group results in modest increases in CB1 affinity (when measured with [³H]CP55,940) and efficacy (discussed later). This suggests that the piperidinyl ring system nitrogen is not likely involved in electrostatic interactions or hydrogen bond formation with the receptor that promotes higher affinity/efficacy.

Figure 2A:
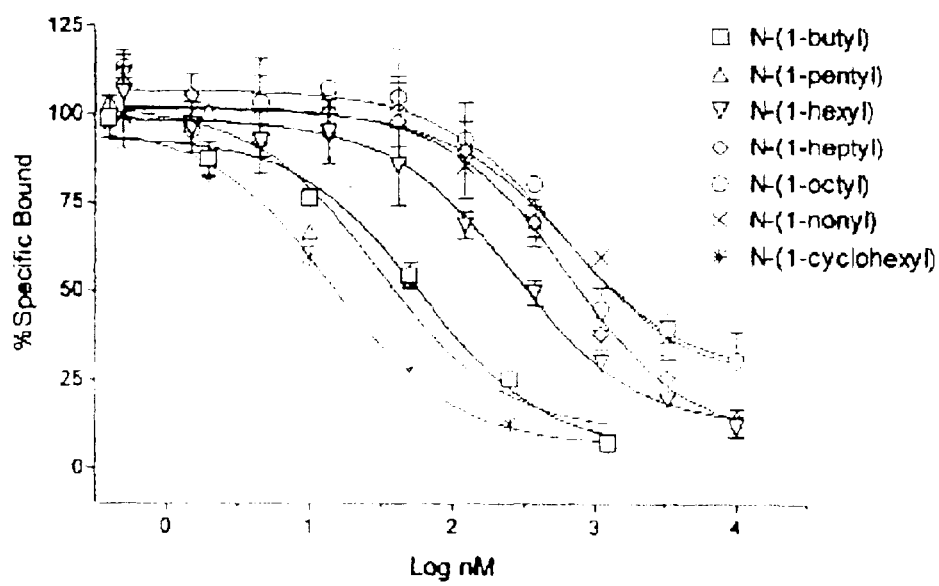
FIGS. 2A–F provide displacement data obtained for various amide analogs of SR141716A, including preferred compounds of the present invention, when competing against [$^3$H]SR1417816A (A), [$^3$H]CP55940 (B) and [$^3$H]WIN55212-2 (C) for CB1 receptor sites in rat brain membrane preparations, or in a human CB1 receptor transfected cell line against [$^3$H]SR1417816A (D), [$^3$H]CP55940 (E) and [$^3$H]WIN55212-2 (F).
Figure 2B:
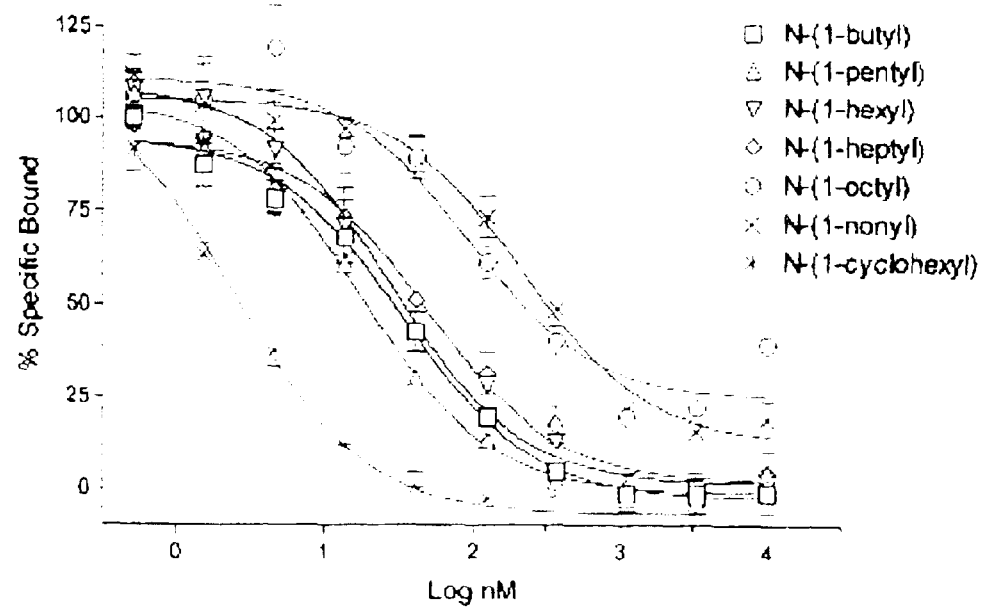
Figure 2C:
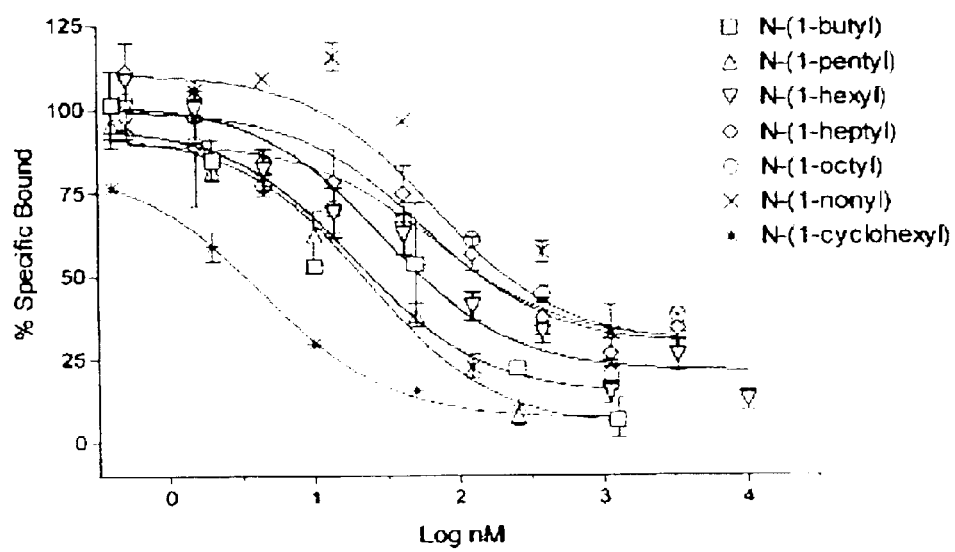
Figure 2:
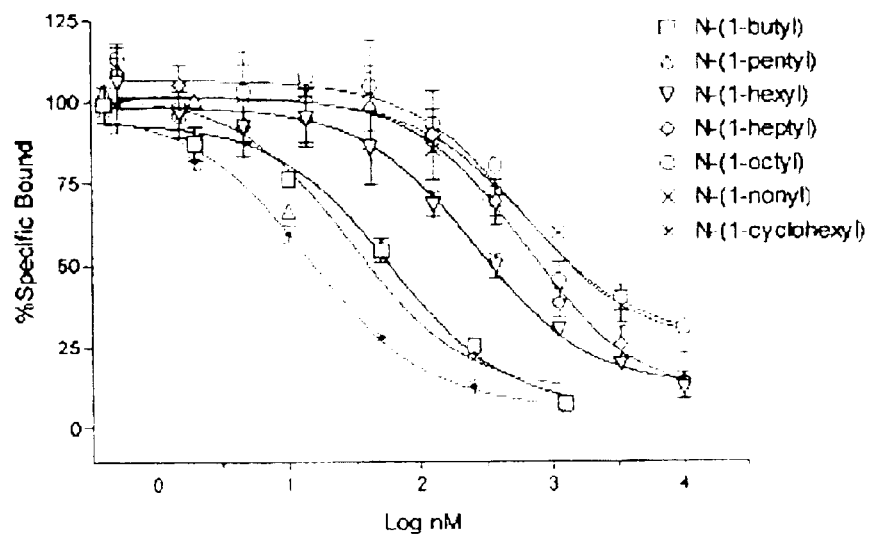
Figure 2:
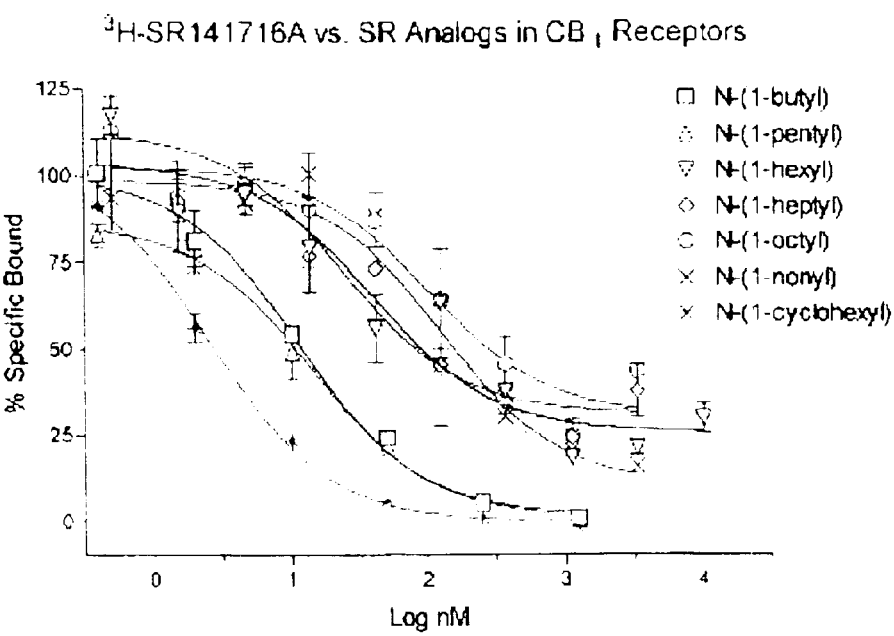

One can see that there is reasonable correspondence between the affinities determined with [³H]CP55,940 and [³H]SR141716A (correlation coefficient (r)=0.97). However, when these compounds were tested for their ability to displace [³H]WIN, quite interesting results were obtained. The data obtained in rat brain suggested that in the alkyl amide series, as the carbon chain extended beyond C5 or C6, both the affinity and the ability to fully displace [³H]WIN55212-2 decreased more rapidly than with [³H]CP55,940 and [³H]SR141716A (FIGS. 2A–C). In addition to these observations, characterization in mouse vas deferens studies with WIN55212-2 also indicated that these compounds were pharmacologically unique (described in greater detail below).

Figure 2F:
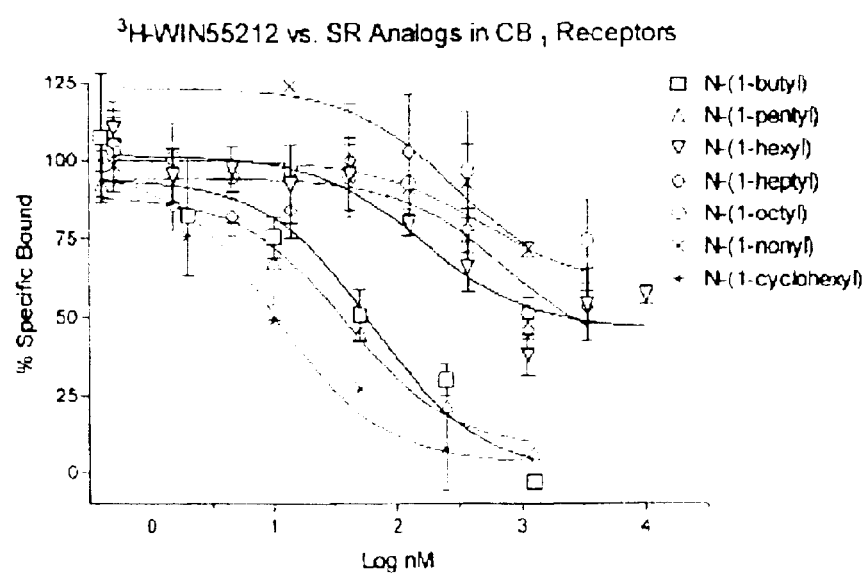

Human CB1 receptor affinity. The alkyl amide analogs of the present invention were examined using transfected cell lines expressing the human CB1 receptor (Table 3). These studies showed an even greater discrepancy in the ability of these compounds to displace [³H]WIN55212-2 as compared to either [³H]CP55,940 or [³H]SR141716A (see FIGS. 2D–F) than was observed in rat brain. It is interesting to note that there is a structural trend where systematic increases in the alkyl side chain length past C6 leads to a slow decrease in affinity and % maximum displacement for [³H]SR141716A, a more rapid loss of affinity and % maximum displacement with [³H]CP55,940, and an extremely rapid and profound loss of affinity and displacing ability with [³H]WIN. The difference between the rat brain membrane preparation and the human CB1 receptor transfects is quite amazing when one considers that these two CB1 receptors possess approximately 99% homology in their sequences.

by LC/UV/MS. The results of the receptor binding assays in these compounds are provided in Tables 4 and 5. It is important to note that while the concentration may have

TABLE 3

Amide Analogs at the 3-Position - Displacement of Various Radioligands in Human CB1 Receptor-Transfected Cells

| Compound | Substituted Group | $^3$H-CP55940 | | | $^3$H-SR141716A | | | $^3$H-WIN55212-2 | | |
|---|---|---|---|---|---|---|---|---|---|---|
| | | $K_i$ (nM) | SEM | Max. Disp. % | $K_i$ (nM) | SEM | Max. Disp. % | $K_i$ (nM) | SEM | Max. Disp. % |
| SR141716A | | 39.2 | a | 79.5 | 2.43 | a | 85.7 | | | |
| SH9631-56 | pyrazole ethyl ester (intermediate) | 44.8 | a | 91.0 | | | | | | |
| MF9725-54C | N-(1-ethyl) | 137 | 19.9 | 66.7 | 35.1 | 1.3 | 95.3 | 185 | 137 | 78.8 |
| MF9725-55C | N-(1-propyl) | 33.7 | 3.2 | 81.9 | 6.0 | 2.6 | 93.4 | 25.1 | 4.6 | 73.3 |
| MF9725-64-17 | N-(1-butyl) | 28.0 | 1.3 | 90.2 | 4.79 | 0.89 | 97.4 | 29.8 | 15.6 | 93.2 |
| MF9725-67-17 | N-(1-pentyl) | 14.6 | 3.6 | 87.1 | 6.35 | 2.4 | 89.9 | 18.7 | 5.9 | 89.9 |
| MF9725-132-25 | N-(1-hexyl) | 124 | 27.4 | 85.6 | 23.5 | 16.5 | 75.4 | 85.4 | 18.6 | 52.7 |
| MF9725-133-25 | N-(1-heptyl) | 29.1 | 69.7 | 85.3 | 9.3 | 1.1 | 67.9 | 393 | 154 | 53.4 |
| MF10110-119-11 | N-[1-(1,1-dimethylheptyl)] | 32.7 | 10.4 | 91.1 | 5.0 | 0.51 | 99.9 | 14.4 | 1.0 | 86.5 |
| MF9879-164-28 | N-(1-octyl) | 288 | 48.0 | 70.6 | 44.7 | 18.6 | 67.8 | 267 | 36.9 | 35.2 |
| MF10110-10-21 | N-(1-nonyl) | 307 | 40.7 | 68.8 | 56.5 | 25.7 | 86.9 | 3553 | 2826 | 28.3 |
| MF9725-68-10 | N-(2-methylpropyl) | 93.6 | 87.6 | 70.1 | 14.3 | 2.4 | 99.5 | 127 | 70.5 | 100 |
| MF9725-65-11 | N-(2-propyl) | 91.0 | 37.3 | 85.4 | 14.4 | 0.23 | 100 | 692 | 666 | 93.6 |
| MF9725-66-11 | N-(1-cyclohexyl) | 7.06 | 0.76 | 92.3 | 1.02 | 0.22 | 99.9 | 5.36 | 0.24 | 96.8 |
| MF9725-178-32 | N-(1-butyl hydrazide) | 175 | 41.6 | 91.1 | 25.1 | 13.3 | 96.4 | 150 | 136 | 76.4 | a n = 1

Further evidence of the unique nature of long chain alkyl analogs at this position was afforded through the use of parallel synthesis to rapidly generate more analogs at this position. The purity and yield of the products was assessed by LC/UV/MS. been overestimated by assuming 100% yield, and thus, the affinity of the compounds underestimated, it is the relative displacements of the various radioligands that is of interest in these experiments.

TABLE 4

Amide Analogs at the 3-Position via Parallel Syntheses - Displacement of Various Radioligands in Whole Rat Brain (CB1) Membrane Preparations

| Compound | Substituted Group | $^3$H-CP55940 | | | $^3$H-SR141716A | | | $^3$H-WIN55212-2 | | |
|---|---|---|---|---|---|---|---|---|---|---|
| | | $K_i$ (nM) | SEM | Max. Disp. % | $K_i$ (nM) | SEM | Max. Disp. % | $K_i$ (nM) | SEM | Max. Disp. % |
| SR141716A | | 6.18 | 1.2 | 86.6 | 1.18 | 0.10 | 96.5 | | | |
| SR144528 | | 74.1 | 11.4 | 84.7 | 81.7 | 19.3 | 68.6 | | | |
| COMBI-18 | Diisopropylamine | | | | | | | | | |
| BT-1 | N-(1-decyl) | 92.8 | a | 83.6 | 45 | a | 92.5 | 1393 | a | 67.4 |
| BT-7 | N-(1-undecyl) | 168 | a | 86.4 | 25.5 | a | 83.8 | 278 | a | 90.3 |
| BT-2 | N-(1-dodecyl) | 109 | a | 82.6 | 53.7 | a | 95.6 | 238 | a | 56.5 |
| BT-6 | N-(1-tridecyl) | 492 | a | 79.3 | 172 | a | 97.6 | 495 | a | 80.5 |
| BT-5 | N-(1-tetradecyl) | | | | | | | | | |
| BT-3 | N-(1-hexadecyl) | | | | | | | | | |
| BT-4 | N-(1-octadecyl) | | | | | | | | | |
| AM-54 | N-acetylethylenediamine) | | | | | | | | | |
| AM-11 | N,N-diethylaminoethyleneamine | | | | | | | | | |
| AM-17 | 2-amino-1-methoxypropane | 64.4 | a | 96.2 | 22.8 | a | 94.1 | 22.6 | a | 84.8 |
| AH-1 | 2-amino-3-picoline | | | | | | | | | |
| AM-19 | 2-aminomethylpyridine | | | | | | | | | |
| AM-4 | 2-aminoethylpyridine | | | | | | | | | |
| AM-29 | 4-methoxyphenethylamine | 92.6 | a | 78.8 | 40.7 | a | 95.1 | 24.7 | a | 82.7 |
| AM-52 | Tyramine | 71.4 | a | 84.7 | 29.8 | a | 100 | 326 | a | 94.9 |
| AM-26 | 4-amino-1-methyl-piperidine | | | | | | | | | |
| AM-28 | 4-hydroxy-4-phenyl-piperidine | 113 | a | 97.2 | 41.2 | a | 97.2 | 69.5 | a | 94.4 |
| AN-2 | 4-methoxy-aniline | 91.0 | a | 96.4 | 11.8 | a | 95.4 | 30.4 | a | 85.8 |
| AM-50 | 1,2,3,4-tetrahydroisoquinoline | 194 | a | 88.3 | 44.6 | a | 90.5 | 152 | a | 89.0 |
| AKS-10262-1 | N-(1-methylhexyl) | 10.7 | a | 98.2 | 2.60 | a | 96.5 | 1.84 | a | 89.0 |
| AKS-10262-2 | geranylamine | 48.1 | a | 84.2 | 20.1 | a | 95.7 | 40.5 | a | 89.0 |
| AKS-10262-3 | N-(1-methyldecyl) | 27.1 | a | 83.7 | 9.7 | a | 97.3 | 22.3 | a | 82.4 |
| AKS-10262-4 | N-(1-methylheptyl) | 26.2 | a | 83.9 | 10.8 | a | 91.3 | 5.8 | a | 53.7 |
| AKS-10262-5 | N-(1-ethylhexyl) | 19.6 | a | 89.5 | 8.6 | a | 95.7 | 25.8 | a | 85.1 |
| AKS-10262-6 | N-(1,3-dimethylpentyl) | 9.6 | a | 91.4 | 2.3 | a | 96.3 | 13.7 | a | 89.9 |

TABLE 4-continued

Amide Analogs at the 3-Position via Parallel Syntheses - Displacement of Various Radioligands in Whole Rat Brain (CB1) Membrane Preparations

| Compound | Substituted Group | $^3$H-CP55940 | | | $^3$H-SR141716A | | | $^3$H-WIN55212-2 | | |
|---|---|---|---|---|---|---|---|---|---|---|
| | | $K_i$ (nM) | SEM | Max. Disp. % | $K_i$ (nM) | SEM | Max. Disp. % | $K_i$ (nM) | SEM | Max. Disp. % |
| AKS-10262-7 | N-(1,5-dimethylhexyl) | 8.97 | a | 89.6 | 3.57 | a | 95.1 | 5.76 | a | 87.7 |
| AKS-10262-8 | N-(1,4-dimethylpentyl) | 3.37 | a | 76.6 | 2.81 | a | 96.2 | 28.6 | a | 94.1 |
| AKS-10262-9 | N-(3,3-diphenylpropyl) | 19.9 | a | 90.1 | 5.52 | a | 96.0 | 10.3 | a | 81.1 |
| AKS-10262-10 | 2-(4-chlorophenyl)-1-methylethylamine | 18.4 | a | 88.8 | 2.70 | a | 95.9 | 10.1 | a | 86.1 |
| AKS-10262-11 | 2-(4-fluorophenyl)-1-ethylamine | | | | | | | | | |
| AKS-10262-12 | N-(3-phenylpropyl) | | | | | | | | | |
| AKS-10262-13 | 3-[4-(methylsulfonyl)phenyl]prop-1-en-2-amine | | | | | | | | | |
| AKS-10262-14 | 2-(3,4-dimethoxyphenyl)-1-methylethylamine | | | | | | | | | |
| AKS-10262-15 | 1-methyl-2-phenylethylamine | | | | | | | | | |
| AKS-10262-16 | (±)-2-amino-1-phenylethanol | | | | | | | | | |
| AKS-10262-17 | 2-phenoxyethylamine | | | | | | | | | |
| AKS-10262-18 | 2,2-diphenylethylamine | | | | | | | | | |
| AKS-10262-19 | 2-(4-nitrophenyl)ethylamine | | | | | | | | | | a n = 1

TABLE 5

Amide Analogs at the 3-Position via Parallel Syntheses - Displacement of Various Radioligands in Human CB1 Receptor - Transfected Cells

| Compound | Substituted Group | $^3$H-CP55940 | | | $^3$H-SR141716A | | | $^3$H-WIN55212-2 | | |
|---|---|---|---|---|---|---|---|---|---|---|
| | | $K_i$ (nM) | SEM | Max. Disp. % | $K_i$ (nM) | SEM | Max. Disp. % | $K_i$ (nM) | SEM | Max. Disp. % |
| SR141716A | | 7.8 | 0.3 | 89.90 | 1.05 | 0.1 | 100 | 23.6 | 6.3 | 100 |
| COMBI-18 | Diisopropylamine | | | | | | | | | |
| BT-1 | N-(1-decyl) | 184 | a | 94.5 | 24.6 | a | 95.4 | 63.8 | a | 12.4 |
| BT-7 | N-(1-undecyl) | 45.6 | a | 82.4 | 5.2 | a | 96.9 | 11.7 | a | 54.9 |
| BT-2 | N-(1-dodecyl) | 176 | a | 79.5 | 43.5 | a | 89.8 | 13.8 | a | 31.4 |
| BT-6 | N-(1-tridecyl) | 201 | a | 75.9 | 4.2 | a | 91.3 | 173 | a | 94.9 |
| BT-5 | N-(1-tetradecyl) | | | | | | | | | |
| BT-3 | N-(1-hexadecyl) | | | | | | | | | |
| BT-4 | N-(1-octadecyl) | | | | | | | | | |
| AM-54 | N-acetylethylenediamine) | | | | | | | | | |
| AM-11 | N,N-diethylaminoethyleneamine | | | | | | | | | |
| AM-17 | 2-amino-1-methoxypropane | 39.8 | a | 86.3 | 17.6 | a | 98.7 | 30.9 | a | 96.8 |
| AH-1 | 2-amino-3-picoline | | | | | | | | | |
| AM-19 | 2-aminomethylpyridine | | | | | | | | | |
| AM-4 | 2-aminoethylpyridine | | | | | | | | | |
| AM-29 | 4-methoxyphenethylamine | 56.9 | a | 80.3 | 16.1 | a | 96.3 | 74.5 | a | 100 |
| AM-52 | Tyramine | 106 | a | 96.1 | 13.6 | a | 99.5 | 162 | a | 100 |
| AM-26 | 4-amino-1-methyl-piperidine | | | | | | | | | |
| AM-28 | 4-hydroxy-4-phenyl-piperidine | 52.1 | a | 79.6 | 28.2 | a | 99.2 | 56.9 | a | 100 |
| AN-2 | 4-methoxy-aniline | 220 | a | 62.6 | 101 | a | 87.3 | 128 | a | 68.1 |
| AM-50 | 1,2,3,4-tetrahydroisoquinoline | 57.7 | a | 66.3 | 21.0 | a | 90.4 | 166 | a | 74.6 |
| AKS-10262-1 | N-(1-methylhexyl) | 11.9 | a | 80.7 | 2.02 | a | 95.6 | 54.6 | a | 100 |
| AKS-10262-2 | geranylamine | 26.8 | a | 84.2 | 6.80 | a | 95.7 | 211 | a | 78.3 |
| AKS-10262-3 | N-(1-methyldecyl) | 41.1 | a | 77.7 | 7.0 | a | 90.0 | 22.2 | a | 76.1 |
| AKS-10262-4 | N-(1-methylheptyl) | 26.3 | a | 79.5 | 2.8 | a | 91.5 | — | a | 0.0 |
| AKS-10262-5 | N-(1-ethylhexyl) | 9.6 | a | 91.4 | 3.8 | a | 95.9 | 78.6 | a | 100 |
| AKS-10262-6 | N-(1,3-dimethylpentyl) | 9.4 | a | 86.5 | 2.2 | a | 100 | 23.9 | a | 78.7 |
| AKS-10262-7 | N-(1,5-dimethylhexyl) | 7.39 | a | 82.5 | 2.10 | a | 93.7 | 64.2 | a | 67.9 |
| AKS-10262-8 | N-(1,4-dimethylpentyl) | 13.2 | a | 76.8 | 5.48 | a | 93.6 | 33.2 | a | 91.5 |
| AKS-10262-9 | N-(3,3-diphenylpropyl) | 25.2 | a | 88.1 | 3.28 | a | 96.7 | 16.9 | a | 77.3 |
| AKS-10262-10 | 2-(4-chlorophenyl)-1-methylethylamine | 22.9 | a | 94.8 | 2.38 | a | 100 | 70.2 | a | 65.5 |
| AKS-10262-11 | 2-(4-fluorophenyl)-ethylamine | | | | | | | | | |
| AKS-10262-12 | N-(3-phenylpropyl) | | | | | | | | | |
| AKS-10262-13 | 3-[4-(methylsulfonyl)phenyl]prop-1-en-2-amine | | | | | | | | | |
| AKS-10262-14 | 2-(3,4-dimethoxyphenyl)-1-methylethylamine | | | | | | | | | |
| AKS-10262-15 | 1-methyl-2-phenylethylamine | | | | | | | | | |
| AKS-10262-16 | (±)-2-amino-1-phenylethanol | | | | | | | | | |
| AKS-10262-17 | 2-phenoxyethylamine | | | | | | | | | |
| AKS-10262-18 | 2,2-diphenylethylamine | | | | | | | | | |
| AKS-10262-19 | 2-(4-nitrophenyl)ethylamine | | | | | | | | | |

Figure 3A:
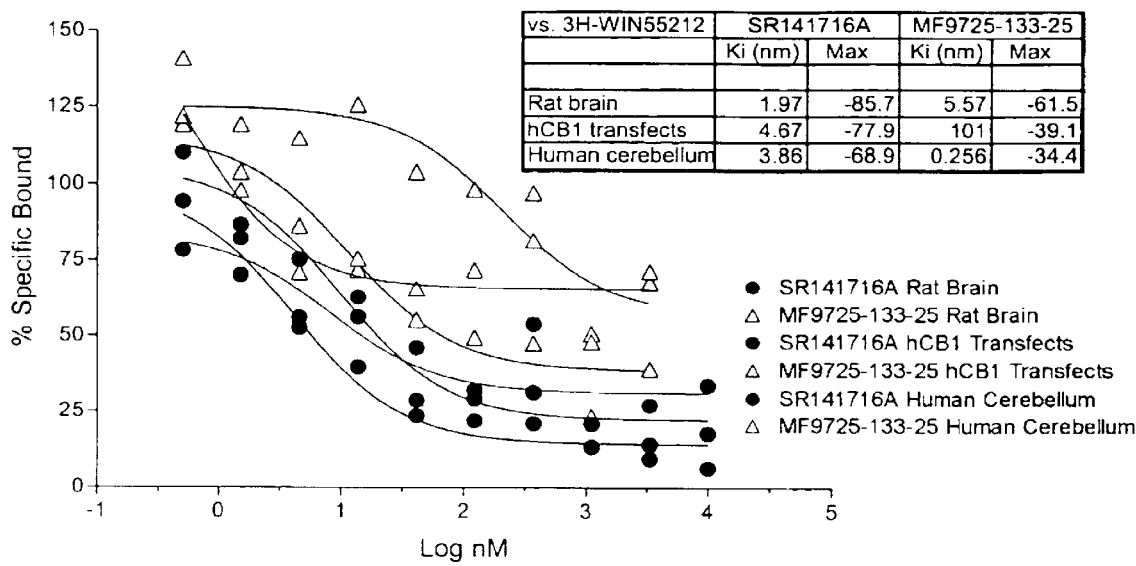
FIG. 3A provides displacement curves for SR141716A and MF9725-133-25 in various cannabinoid receptor preparations.
Figure 3B:
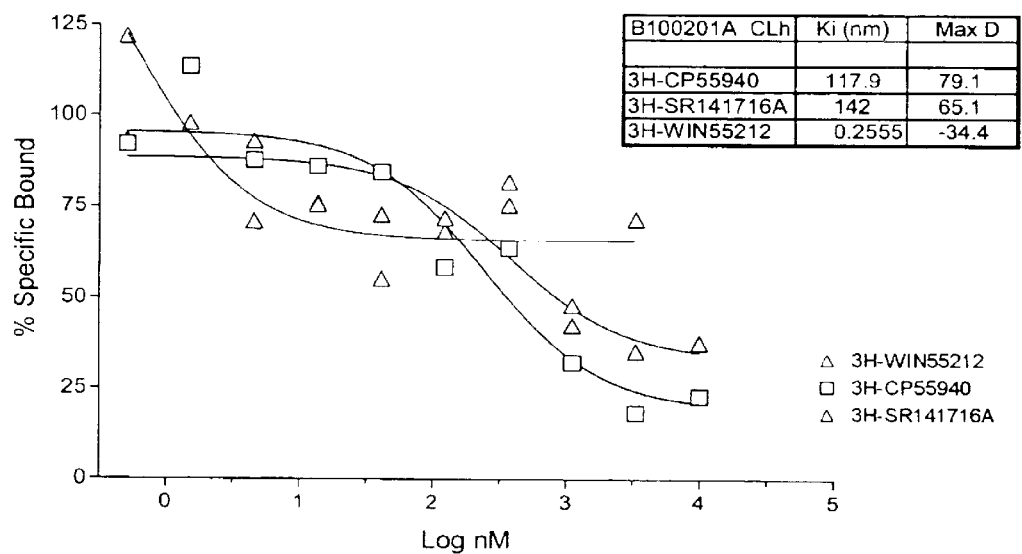
FIG. 3B provides displacement curves for MF9725-133-25 against various radioligands in human cerebellum.

It is possible that the augmentation in these compounds' binding selectivity in human CB1 transfects could be a result of the nature of transfected cell lines, and not due to differences in receptor sequence and structure. However, when these compounds were tested in human brain membrane preparations (cerebellum and cortex) similar results were obtained (see FIGS. 3A–B). Thus, all evidence obtained to date supports the conclusion that these long chain alkyl amides are unique from all other classes of cannabinoid receptor ligands with regard to their ability to displace the various radioligands tested. The data also illustrate that despite a very high degree of sequence homology, the alkyl amides beyond C6 interact at rat and human CB1 receptors quite differently.

Human CB2 receptor affinity. The relative selectivity of the analogs for CB1 versus CB2 receptors varied modestly regardless of the structural modifications examined to date. For example, the most CB1 selective analog MF9725-66-11 (the cyclohexyl analog) had a 93-fold CB1 selectivity, whereas the ethanolamide MF9725-93-31, had only a 10-fold preference for the CB1 binding site (Tables 6 and 7).

TABLE 6

Amide Analogs at the 3-Position - Displacement of $^3$H-CP55,940 in Human CB2 Receptor-Transfected Cells

| | | $^3$H-CP55940 | | |
|---|---|---|---|---|
| Compound | Substituted Group | $K_i$ (nM) | SEM | Max. Disp. % |
| SR141716A | | 313 | a | |
| SR144528 | | 4.92 | 0.39 | 88.4 |
| MF9725-9D | precursor - diketone | nr | nr | 0.0 |
| SH9631-55 | pyrazole acid (intermediate) | nr | nr | 0.0 |
| SH9631-56 | pyrazole ethyl ester (intermediate) | 4397 | 247 | 51.4 |
| MF9725-54C | N-(1-ethyl) | 3114 | 613 | 59.6 |
| MF9725-55C | N-(1-propyl) | 2957 | 2097 | 68.3 |
| MF9725-64-17 | N-(1-butyl) | 1598 | 425 | 75.6 |
| MF9725-67-17 | N-(1-pentyl) | 1110 | 241 | 75.9 |
| MF9725-132-25 | N-(1-hexyl) | 6873 | a | 66.9 |
| MF9725-133-25 | N-(1-heptyl) | 4027 | 174 | 47.8 |
| MF10110-119-11 | N-[1-(1,1-dimethylheptyl)] | 16555 | 3445 | 52.8 |
| MF9879-164-28 | N-(1-octyl) | 98366 | 92734 | 45.3 |
| MF10110-l0-21 | N-(1-nonyl) | 22878 | 17622 | 53.8 |
| MF9725-68-10 | N-(2-methylpropyl) | 704 | 127 | 80.0 |
| MF9725-65-11 | N-(2-propyl) | 1745 | 576 | 68.3 |
| MF9725-131-25 | N-hydroxy | 7817 | a | 27.0 |
| MF9725-93-31 | N-(2-OH-ethyl) | 4269 | 572 | 33.3 |
| MF9725-94-31 | N-(3-OH-propyl) | 1249 | 279 | 43.1 |
| MF9725-95-31 | N-(4-OH-butyl) | 5716 | a | 54.3 |
| MF9725-105-38 | (+)-N-(2-OH-1-methylethyl) | 5898 | 2810 | 47.5 |
| MF9725-106-39 | (−)-N-(2-OH-1-methylethyl) | 1767 | 142 | 52.1 |
| MF9725-33D | N-morpholin-4-yl | 2405 | 777 | 54.5 |
| MF9725-66-11 | N-(1-cyclohexyl) | 228 | 1.5 | 84.5 | a n = 1
nr = no displacement at concentrations tested

TABLE 7

Hydrazide Analogs at the 3-Position - Displacement of $^3$H-CP55,940 in Human CB2 Receptor-Transfected Cells

| | | $^3$H-CP55940 | | |
|---|---|---|---|---|
| Compound | Substituted Group | $K_i$ (nM) | SEM | Max. Disp. % |
| SR141716A | | 313 | a | |
| SR144528 | | 4.92 | 0.39 | 88.4 |
| MF9879-34-8 | N-hydrazide | 12060 | 170 | 80.8 |
| MF9879-47-23 | N-(1-methyl hydrazide) | 6660 | 925 | 85.6 |
| MF9879-48-11 | N-(1-ethyl hydrazide) | 6061 | 902 | 91.3 |
| MF9879-7-6 | N-(1-propyl hydrazide) | 2620 | 444 | 91.4 |
| MF9725-179-32 | N-(1-butyl hydrazide) | 2851 | 155 | 92.0 |
| MF9725-181-32 | N-(2-methylpropyl hydrazide) | 2186 | 755 | 93.2 | a n = 1

In general, the majority of those compounds showing a modest increase in selectivity for the CB1 receptor over that of SR141716A were in the alkyl amide and cyclic analogs. The affinities of the hydrazide analogs for CB2 receptors were even lower than that of SR141716A, but their CB1 affinity was even more dramatically reduced. Thus, in this set of compounds, both affinity and selectivity for the CB1 receptor was decreased. However, the majority of the structural modifications did not appear to have a robust effect on CB1/CB2 selectivity, primarily because none of the compounds tested were found to possess high affinity for the CB2 receptor. The absence of CB2 selective ligands in our series of analogs is consistent with the observation that the CB2-selective antagonist SR144528, when compared to SR141716A, has structural modifications in addition to the change at the aminopiperidine moiety that was explored in these studies.

Cannabinoid receptor-mediated alteration in GTP-γ-[$^{35}$S] binding. In addition to assessing CB1 and CB2 receptor affinities, all of the compounds have been screened in the GTP-γ-[$^{35}$S] assay to begin characterization of the compounds as agonists, partial agonists, antagonists or inverse agonists. The results of GTP-γ-[$^{35}$S] studies with the alkyl amide and hydrazide analogs (Tables 8 and 9) demonstrate that, in all instances, these compounds act like antagonists or inverse agonists.

Pharmacological characterization in isolated mouse vas deferens. The results of the assessment of the compounds in the mouse vas deferens (Table 8) support the conclusion that some of the alkyl amide analogs interact with the CB1 receptor in a unique manner. Specifically, one can see from the data in this table for the alkyl amides that as the chain length was increased from the butyl analog to the heptyl analog, the dextral shift in the WIN55212-2 dose response curve was reduced. Indeed, in one experiment the heptyl analog failed to produce an effect on the WIN55212-2 dose response curve, despite this compound having good affinity (46.2 nM vs. [$^3$H]CP55,940), and producing a robust inverse agonist effect in the absence of any application of

TABLE 8

Amide Analogs at the 3-Position-Inverse Agonist/Antagonist Activity

| Compound | Substituted Group | GTP-γ-[$^{35}$S] in Whole Rat Brain | | | Mouse Vas Deferens Tissue Assay (WIN55212-2 as agonist) | | |
|---|---|---|---|---|---|---|---|
| | | EC$_{50}$ (NM) | SEM | E$_{max}$ | K$_b$ (nM) | Dextral Shift | % Inverse Effect |
| SR141716A | | 56305 | 14330 | −37.8 | 0.4 | 81.4 | 65.2 |
| SR144528 | | 8136 | 258 | −27.7 | | | |
| SH9631-56 | Pyrazole ethyl ester (intermediate) | 195$^c$ | 89.8$^c$ | −18.4$^c$ | | | |
| MF9725-54C | N-(1-ethyl) | 30275 | 5005 | −46.9 | | | |
| MF9725-55C | N-(1-propyl) | 11140 | 3721 | −35.7 | | | |
| MF9725-64-17 | N-(1-butyl) | 8536 | 3134 | −38.5 | 21.2 | no effect | 28.2 |
| NF9725-67-17 | N-(1-pentyl) | 5270 | 1656 | −7.4 | 31.7 | 11.0 | 86.6 |
| MF9725-132-25 | N-(1-hexyl) | 29375 | 16135 | −13.0 | 15.4 | no effect | 30.1 |
| MF9725-133-25 | N-(l-heptyl) | 212950 | 3950 | −20.0 | no effect, 83.9$^b$ | no effect, 1.5$^b$ | 50.6, 37.8$^b$ |
| MF9879-164-28 | N-(1-octyl) | 676800$^a$ | 187400 | −21.3 | | | |
| MF10110-10-21 | N-(1-nonyl) | 293500 | 60400 | −20.1 | | | |
| MF9725-68-10 | N-(2-methylpropyl) | 7536 | 8.5 | −11.0 | | | |
| MF9725-65-11 | N-(2-propyl) | 15990 | 4670 | −46.4 | | | |
| MF9725-93-31 | N-(2-OH-ethyl) | 1669000$^a$ | 658000 | −76.5 | | | |
| MF9725-94-31 | N-(3-OH-propyl) | 240700 | 39200 | −83.3 | | | |
| MF9725-95-31 | N-(4-OH-butyl) | 303900 | 131300 | −79.5 | | | |
| MF9725-105-38 | (+)-N-(2-OH-1-methylethyl) | 293900 | 11700 | −83.8 | | | |
| MF9725-106-39 | (−)-N-(2-OH-1-methylethyl) | 291850 | 43450 | −83.0 | | | |
| MF9725-33D | N-morpholin-4-yl | 38870 | 28360 | −76.3 | 12.5 | 26.3 | 82.5 |
| MF9725-66-11 | N-(1-cyclohexyl) | 26030 | — | −22.1 | 1.2 | 26.7 | 55.5 |

$^a$= Value is above highest concentration on displacement curve
$^b$= Due to unexpected result, compound was assayed again and both replicates are shown
$^c$= Assay was run in CB1 (human) clone receptors

TABLE 9

Hydrazide Analogs at the 3-Position-Inverse Agonist/Antagonist Activity

| Compound | Substituted Group | GTP-γ-[$^{35}$S] in Whole Rat Brain | | | Mouse Vas Deferens Tissue Assay (WIN55212-2 as agonist) | | |
|---|---|---|---|---|---|---|---|
| | | EC$_{50}$ (NM) | SEM | E$_{max}$ | Kb (nM) | Dextral Shift | % Inverse Effect |
| MF9725-179-32 | N-(1-butyl hydrazide) | 127900 | 18900 | −72.7 | | | |
| MF9725-181-32 | N-(2-methylpropyl hydrazide) | 73585 | 20325 | −78.1 | | | |
| MF9879-7-6 | N-(1-propyl hydrazide) | 104895 | 17505 | −85.0 | | | |
| MF9879-34-8 | N-hydrazide | 419350$^b$ | 53150 | −71.7 | | | |
| MF9879-48-11 | N-(1-ethyl hydrazide) | 494800$^b$ | 161500 | −81.4 | | | |
| MF9879-47-23 | N-(1-methyl hydrazide) | 12030000$^b$ | a | −63.8 | | | |
| MF9879-64-23 | 2,4-deschloro-1-phenyl | 361300 | a | −47.2 | | | |
| MF9879-117-24 | des-2,4-chlorophenyl-1-cyclohexyl | 108100 | 100 | −71.7 | | | |
| MF10278-22-16 | 1-hexyl | 74710 | 1450 | −71.5 | | | |
| MF10278-20-15 | 1-heptyl | 156050 | 14450 | −85.7 | | | | a n = 1
$^b$= value is above highest concentration on displacement curve

This observation is consistent with the antagonist conferring region involving the 2,4-dichlorophenyl ring, and not the piperidine carboxy amide region of importance in the compounds of the present invention.

WIN55212-2. Thus, the data suggest that this compound can interact at the receptor (displace [$^3$H]CP55,940 and [$^3$H]SR141716A) and produce inverse agonist effects, but not compete for the WIN55212-2 binding site, and thereby fail to produce a dextral shift in the WIN55212-2 dose response curve. This lends pharmacological significance to the aforementioned "WIN-sparing" displacement curves (FIG. 1) obtained with the alkyl amide analogs.

Methods—membrane preparation from brain. The methods for tissue preparation are essentially those described by Devane et al. (1988) as modified by Compton et al. (1993) and later by Thomas et al. (1998). Whole rat brains or dissected regions from live CD rats from Charles River or Pel-Freez Biologicals (Rogers, Ark.), or human brain sections obtained from the National Disease Research Institute, were allowed to thaw to room temperature on ice. Both whole brain and dissected brain regions were used because different brain regions may express different cannabinoid receptor subtypes (Skaper et al., 1996; Thomas et al., 1998). The tissue was homogenized with a Kontes Potter-Elvehjem glass-Teflon grinding system (Fisher Scientific, Springfield, N.J.) in buffer 1 (320 mM sucrose, 2 mM EDTA, 5 mM $MgCl_2$. The homogenate was centrifuged at 1600 g for 10 min. The supernatant was saved and combined with the two subsequent supernatants obtained from washing and 1600 g centrifugation of the P1 pellet. The combined supernatant fractions were then centrifuged at 39,000 g for 15 min. The P2 pellet was resuspended in 50 mL of buffer 2 (50 mM Tris.HCl, 2 mM EDTA, 5 mM $MgCl_2$, pH 7.0), incubated at 37° C. for 10 min, then centrifuged at 23,000 g for 10 min. The P2 membrane was resuspended in 50 mL of buffer 2, incubated at 30° C. for 40 min, then centrifuged at 11,000 g for 15 min. The final wash-treated P2 pellet was resuspended in assay buffer 3 (50 mM Tris.HCl, 1 mM EDTA, 3 MM $MgCl_2$, pH 7.4). Protein concentrations were determined by the method of Bradford (1976) using Coomassie brilliant blue dye (Bio-Rad, Richmond, Calif.) and BSA standards (bovine serum albumin, fatty acid free, Sigma Chemical Co., St. Louis, Mo.) prepared in assay buffer 3. The membrane preparation was divided into aliquots and stored at −80° C. For use in the binding assay, an aliquot of frozen membranes was thawed on ice and diluted to a concentration of ca. 0.2 mg/mL in assay buffer.

Methods—binding assay in brain membrane preparation. The methods for ligand binding are essentially those described by Devane et al. (1988) with the exception that we used a filtration assay. Binding was initiated by the addition of 20 μg of P2 membrane to test tubes containing [$^3$H]CP-55,940 (ca. 130 Ci/mmol), [$^3$H]SR141716A (ca. 22.4 Ci/mmol), or [$^3$H]WIN55212-2 (ca. 50 Ci/mmol) a cannabinoid analog (for displacement studies), and a sufficient quantity of buffer A (50 mM Tris.HCl, 1 mM EDTA, 3 mM $MgCl_2$, 5 mg/mL BSA, pH 7.4) to bring the total incubation volume to 0.5 mL. In the displacement assays, the concentrations of [$^3$H]CP-55,940, [$^3$H]SR141716A and [$^3$H] WIN55212-2 were 7.2 nM, 20 nM, and 2.48 nM, respectively. Nonspecific binding was determined by the inclusion of 10 μM unlabeled CP-55,940, SR141716A, or WIN55212-2. All cannabinoid analogs were prepared by suspension in buffer A from a 1–5 mg/mL ethanolic stock. Following incubation at 30° C. for 1 h, binding was terminated by vacuum filtration through pretreated filters in a 96-well sampling manifold (Millipore, Bedford, Mass.). Reaction vessels were washed at least 3 times with 1 mL of ice cold buffer B (50 mM Tris.HCl, 1 mg/mL BSA). The filter plates were air-dried and sealed on the bottom. Liquid scintillant was added to the wells and the top sealed. After incubating the plates in cocktail for at least 2 h, the radioactivity present was determined by liquid scintillation spectrometry. Assays were done in duplicate, and results represent the combined data of three to six independent experiments. All assays were performed in polypropylene test tubes. The GF/C glassfiber filter plates (Packard, Meriden, Conn.) were pretreated in buffer B for at least 1 h.

Methods—binding assay in transfected cell lines. The methods used for performing binding assays in transfected cells expressing human CB1 or CB2 receptors are those used above. The CB1 receptor involved a HEK-293 expression system whereas the CB2 receptor was expressed in CHO-K1 cells. Binding was initiated with the addition of 40 pM of cell membrane protein to assay tubes containing [$^3$H]CP-55,940, [$^3$H]SR141716A or [$^3$H]WIN55212-2, a cannabinoid analog (for displacement studies), and a sufficient quantity of buffer A (50 mM Tris.HCl, 1 mM EDTA, 3 mM $MgCl_2$, 5 mg/mL BSA, pH 7.4) to bring the total incubation volume to 0.5 mL. The incubations and separations were then performed as described above for rat brain membrane preparations.

Data analysis. Saturation and displacement data were analyzed by unweighted nonlinear regression of receptor binding data. For displacement studies, curve-fitting and $IC_{50}$ calculation were done with GraphPad Prism (GraphPad Software, Inc., San Diego, Calif.), which fits the data to one and two-site models and compares the two fits statistically. A similar approach was used for the analysis of isotherm data for calculation of $K_d$'s. A two-site fit was accepted only if it was statistically significant (p<0.05) and the following results were not observed:

1. The two $IC_{50}$ values were almost identical with a two-site model.
2. One of the $IC_{50}$ values was outside the range of the displacement data.
3. One of the sites had a very small fraction of receptors.
4. The best-fit values for the plateaus differed from the ranges observed in the displacement data.

$IC_{50}$ values were then converted to $K_i$ values by reported methods (Cheng and Prusoff, 1973). The statistical evaluation of curve-fitting data allowed for a non-arbitrary conclusion based on the displacement data.

b. GTP-γ-[$^{35}$S] Binding Assay.

Introduction. The purpose of this assay was to characterize the functional activity of lead compounds identified by the radioligand competition binding assays described above. Data from the GTP-γ-[$^{35}$S] binding assay was used to determine if a compound was an agonist, antagonist or inverse agonist at G-protein-linked cannabinoid receptors. Agonist binding to a G-protein-linked receptor results in an increased affinity of the G-protein α-subunit for GTP relative to GDP. Eventually, an active αGTP complex forms to complete the stimulus-effector coupling. The α-subunit has intrinsic GTPase activity which generates a free α-subunit which can recombine with the β- and γ-subunits readying the G-protein for another signal transduction cycle. In the current assay, GTP-γ-[$^{35}$S] cannot be hydrolyzed by the α-subunit. Thus, the amount of bound GTP-γ-[$^{35}$S] is a marker for G-protein activation. In this assay, an agonist increases basal GTP-γ-[$^{35}$S] binding, an inverse agonist decreases basal binding and basal binding would be unaffected by an antagonist.

Experimental Design. The specific binding of GTP-γ-[$^{35}$S], in the absence of test compound, was termed "basal" activity. Test compounds were characterized as agonist, antagonist, or inverse agonist based on their effect on basal activity. The effect of 0.1, 1.0, or 10 μM test compound on basal activity was used to determine its potential effects on G-protein-mediated signal transduction. The concentrations spanned two orders of magnitude because affinity may not be related to efficacy. This is especially true in the case of G-protein-linked receptors (Kenakin 1996). Effects of the test compounds are reported as the percent change from basal. More thorough dose-response analysis may be run to determine, for example, if a compound is a full or partial agonist.

Methods. Binding was determined using membrane homogenates from whole brain The assays were conducted as previously described (Sim et al. 1996) on brain tissue prepared as described above. In a final volume of 0.5 mL, each assay tube contained: 0.02 mg crude membrane homogenate (0.1 mL), 200 $\mu$M GDP (0.05 mL; to reduce basal G-protein activity), 0.1 nM GTP-$\gamma$-[$^{35}$S] (0.05 mL) and several concentrations of test compound (0.05 mL) or an equivalent volume of vehicle (used for determination of total binding). Nonspecific binding was determined in the presence of 100 $\mu$M unlabeled GTP-$\gamma$-S (0.05 mL). Duplicate samples were incubated for 1 h at 30° C. Since this assay is amenable for use with high throughput screening methods, the binding assays were run using a 96-well plate format. Specific binding was calculated as total binding-nonspecific binding.

c. In situ Testing in Mouse Isolated Vas Deferens

Introduction. The mouse isolated vas deferens can be used to determine both the potency and efficacy (maximum degree of inhibition produced) of cannabinoid receptor agonists. Because of its high sensitivity, this assay usually requires only microgram quantities of test material. Using SR141716A, the assay can also be used to distinguish between agonists for cannabinoid CB1 receptors and agonists for other receptor types. Finally, the assay can be used to evaluate the ability of antagonists and inverse agonists to block the inhibitory effects of cannabinoid receptor agonists on evoked contractions of the mouse vas deferens (Pertwee et al., 1995a). It is this assessment that might be the most valuable test in order to further characterize the "WIN-sparing" alkyl amide analogs of the present invention.

The inhibitory effect of cannabinoids on electrically evoked contractions is thought to be mediated by cannabinoid receptors located on prejunctional neurones rather than on the smooth muscle. Thus cannabinoids can inhibit electrically evoked contractions without affecting the contractile responses to the main junctional transmitters of the vas deferens, noradrenaline and ATP (Pertwee and Griffin, 1995). Direct measurements of cannabinoid effects on evoked transmitter release from vasa deferentia have been reported (Ishac et al., 1996). CB1 activation by $\Delta^9$-THC or anandamide inhibits electrically evoked noradrenaline release and is blocked by SR141716A.

Experimental design. Isolated mouse vasa deferentia were used to determine the potency and efficacy of test compounds as inhibitors of electrically evoked contractions. Alternatively, test analogs were tested for their ability to block the inhibitory effect of cannabinoid agonists, depending upon the results in the GTP-$\gamma$-[$^{35}$S] assay. Ability to antagonize was expressed in terms of the association constant ($K_b$) for the forward reaction between antagonist and cannabinoid receptors. $K_b$ was evaluated by constructing agonist concentration-response curves both in the presence of an antagonist and in its absence, calculating the magnitude of shifts in agonist concentration-response curves induced by the antagonist (see below) and then applying the Schild equation (Pertwee et al., 1995a). To explore the susceptibility of test compounds (e.g., amide and hydrazide analogs described above) to amide hydrolysis, some experiments were done with the myenteric plexus preparation of guinea pig small intestine, which also serves as a cannabinoid bioassay (Pertwee et al., 1992) but which, unlike the mouse vas deferens, seems to have amidase activity (Pertwee et al., 1995d). These experiments were done in the presence and absence of an amidase inhibitor such as phenylmethylsulphonylfluoride (PMSF), previous experiments having shown that the inhibitory effect of anandamide on electrically evoked contractions of the myenteric plexus preparation can be markedly potentiated by PMSF (Pertwee et al., 1995d). Cannabinoids lacking an amide group were not potentiated by PMSF.

Methods. The mouse isolated vas deferens and guinea pig myenteric plexus preparations were set up for field stimulation in 4-mL organ baths containing Krebs-Henseleit solution as described previously (Pertwee et al., 1992; Abadji et al., 1994; Pertwee et al., 1993). Electrical field stimulation was between platinum electrodes located at the upper and lower ends of each bath. The stimuli were generated by a Grass S48 stimulator, then amplified (Med-Lab channel attenuator) and finally divided to yield separate outputs to four organ baths (Med-Lab Stimusplitter). All contractions were recorded isometrically.

Concentration-response curves were constructed cumulatively. Drug concentrations producing a 50% reduction in the amplitude of electrically evoked contractions ($IC_{50}$ values) were calculated by nonlinear regression analysis using GraphPAD InPlot (GraphPAD Software, San Diego). The statistical significance and magnitude of shifts in concentration-response curves of agonists induced by antagonists were evaluated by analysis of variance (applying the technique of 4-point or 6-point assay; Colquhoun, et al., 1971).

All test compounds were stored at $-20°$ C. and protected from white light at all times. The vehicle was Tween/saline. Preparation of Ring-Constrained Analog of SR141716A (Formula III wherein R is N-piperidinyl)

General Procedures: Acetonitrile was degassed and kept under N2 before use. The quartz tube utilized (200×38 mm, 24/40 joint) was evacuated and back-filled with N2 several times before addition of solution.

A solution of SR141716A [(lot # DFB-8050-34(73–97)), 13.48 mg in 3.0 mL acetonitrile, 9.49 mM] was placed in a quartz tube, sealed with a rubber septum and purged with N2 prior to irradiation. The tube was suspended approximately 8 inches away from a water-cooled quartz immersion well containing a 450-W high-pressure Hg lamp (Hanovia). The course of reaction was monitored by taking 250 mL aliquots after 5, 10, 20, 40, 80 and 120 minutes. The total time of irradiation: 150 minutes. The aliquots were analyzed by HPLC (Waters Nova-Pak C18 4 mm, 8×100 mm RCM; eluant 25% H2O-75% CH3CN) and analytical tlc (Si gel 60, eluant 1:1 hexanes-EtOAc, visualized by uv, PMA/Ce(SO4) 2). The bright yellow liquid was decanted away from the acetonitrile-insoluble orange residue, and the weight of both were determined.

Theoretical Yield=12.42 mg, 0.029 mmol

Percent Yield=[(3.3+1.9 mg)/12.42 mg]*100=41.9% yield

The compound was characterized by a variety of 1-D and 2-D NMR experiments (1H, 13C, COSY, ROESY, HSQC, HMBC) as well as by LC/MS.

LC/MS 449.2 (100) [M+Na], 427.0 (63.1) [M+1], 327.1 (74.1), 263.1 (17.4).

LITERATURE CITED

ABADJI, V.; LiN, S.; TAHA, G.; GRIFFIN, G.; STEVENSON, L. A.; PERTWEE, R. G. AND MAKRIYANNIS, A.: (R)-Methandamide: A Chiral Novel Anandamide Possessing Higher Potency and Metabolic Stability. J. Med. Chem. 37:1889–1893, 1994.

ACETO, M. D., SCATES, S. M., LOWE, J. A. AND MARTIN, B. R.: Cannabinoid precipitated withdrawal by the selective cannabinoid receptor antagonist, SR141716A. Eur. J. Pharmacol. 282:R1-R2, 1995.

ADAMS, R., HARFENIST, M., AND LOEWE, S.: New analogs of tetrahydrocannabinol. XIX. J. Am. Chem. Soc. 71:1624–1628, 1949.

ADAMS, R., MACKENZIE, S. J., AND LOEWE, S.: Tetrahydrocannabinol homologs with doubly branched alkyl groups in the 3-position. XVIII. J. Am. Chem. Soc. 70:664–668, 1948.

ADAMS, I. B., COMPTON, D. R., AND MARTIN, B. R.: Assessment of anandamide interaction with the cannabinoid brain receptor: SR 141716A antagonism studies in mice and autoradiographic analysis of receptor binding in rat brain. J. Pharmacol. Exp. Ther. 284 (3): 1209–17, 1998.

ADKINS, H., AND REEVE, E. W.: A Synthesis of dl-Threonine. J. Am. Chem. Soc. 60: 1328–1331, 1938.

ASHTON, W. T. AND Doss, G. A.: A regioselective route to 3-alkyl-1-aryl-1H-pyrazole-5-carboxylates: synthetic studies and structural assignments. J. Heterocycl. Chem. 30:307–311, 1993.

BARG, J., FRIDE, E., HANUS, L., LEVY, R., MATUS-LEIBOVITCH, N., HELDMAN, E., BAYEWITCH, M., MECHOULAM, R. AND VOGEL, Z.: Cannabinomimetic behavioral effects of and adenylate cyclase inhibition by two new endogenous anandamides. Eur. J. Pharmacol. 287:145–152, 1995.

BARTH, F., CASELLAS, P., CONGY, C., MARTINEZ, S., RINALDI, M., ANNE-ARCHARD, G.: Preparation of N-piperidino-5-(4-chlorophenyl)-1-(2,4-dichlorophenyl)-4-methylpyrazole-3-carboxamide. Eur. Pat. Appl.: EP-94-402717, 12 pp., 1995a.

BARTH, F., CASELLAS, P., CONGY, C., MARTINEZ, S., RINALDI, M., AND ANNE-ARCHARD, G.: Preparation of N-piperidino-5-(4-chlorophenyl)-1-(2,4-dichlorophenyl)-4-methylpyrazole-3-carboxamide as a cannabinoid receptor antagonist. In Eur. Pat. Appl., pp. 12 pp., (Sanofi, Fr.)., EP, 1995b.

BARTH, F., CASELLAS, P., CONGY, C., MARTINEZ, S., RINALDI, M.: Preparation of 1,5-diphenyl-3-pyrazolecarboxamide derivatives with cannabinoid receptor affinity. Eur. Pat. Appl.: EP-94-402890, 22 pp., 1997.

BARTH, F., RINALDI-CARMONA, M., MILLAN, J., DEROCQ, J.-M., BOUABOULA, M., CASELLAS, P., CONGY, C., OUSTRIC, D., SARRAN, M., CALANDRA, B., PORTIER, M., SHIRE, D., BRELIRE, J. C. AND LE FUR, G.: SR 144528, a potent and selective antagonist of the CB2 receptor. International Cannabis Research Society abstract, to be presented June, 1997.

BARTH, F., CASELLAS, P., MILLAN, J., OUSTRIC, D., RINALDI, M., AND SARRAN, M.: 3-pyrazolecarboxamide derivatives having cannabinoid receptor affinity. In PCT Int. Appl., pp. 99 pp., (Sanofi, Fr.; Barth, Francis; Casellas, Pierre; Millan, Joseph; Oustric, Didier; Rinaldi, Murielle; Sarran, Martine)., WO, 1997a.

BARTH, F., CONGY, C., MARTINEZ, S., AND RINALDI, M.: Preparation of N-piperidinopyrazole-3-carboxamides and analogs as cannabinoid receptor antagonists. In PCT Int. Appl., pp. 37 pp., (Sanofi, Fr.; Barth, Francis; Congy, Christian; Martinez, Serge; Rinaldi, Murielle)., WO, 1997b.

BARTH, F., CONGY, C., MARTINEZ, S., AND RINALDI, M.: Preparation and formulation of tricyclic heterocycles containing a pyrazole-3-carboxamide subunit for pharmaceutical use as cannabinoid receptor antagonists. In PCT Int. Appl., pp. 29 pp., (Sanofi-Synthelabo, Fr.)., WO, 2001a.

BARTH, F., MILLAN, J., OUSTRIC, D., RINALDI, M., AND VERNHET, M.: Preparation and formulation of tricyclic heterocycles containing a 1-benzylpyrazole-3-carboxamide subunit for pharmaceutical use as cannabinoid receptor antagonists. In PCT Int. Appl., pp. 35 pp., (Sanofi-Synthelabo, Fr.)., WO, 2001b.

BAYEWITCH, M., AVIDOR-REISS, T., LEVY, R., BARG, J., MECHOULAM, R. AND VOGEL, Z.: The peripheral cannabinoid receptor: adenylate cyclase inhibition and G protein coupling. FEBS Lett. 375:143–7, 1995.

BEARDSLEY, P. M., SCIMECA, J. A., AND MARTIN, B. R.: Studies on the agonistic activity of $\Delta^{9,11}$-THC in mice, dogs and rhesus monkeys and its interactions with delta 9-tetrahydrocannabinol. J. Pharmacol. Exp. Ther. 241:521–6, 1987.

BEGLEY, W. J., GRIMSHAW, J., AND TROCHA-GRIMSHAW, J.: Pyrazolo[1,5-f]phenanthridine and Derivatives: Electrochemical and Photochemical Synthesis. Journal of the Chemical Society, Perkin Transactions 1 1974: 2633–2637, 1974.

BLANCHARD, J. C., AND MENARD, F.: Use of central cannabinoid receptor antagonist for preparing medicines designed to facilitate smoking cessation. In PCT Int. Appl., pp. 11 pp., (Sanofi-Synthelabo, Fr.)., WO, 2001.

BLOMQUIST, AND BALDWIN: J. Am. Chem. Soc. 70: 29, 1948.

BORCH, R. F., BERNSTEIN, M. D., AND DURST, H. D.: The cyanohydridoborate anion as a selective reducing agent. J. Am. Chem. Soc. 93:2897–2904, 1971.

BRADFORD, M. M.: A rapid and sensitive method for the quantitation of microgram quantities of protein utilizing the principle of protein-dye binding. Anal. Biochem. 72:248–254, 1976.

BRANDSMA, L. AND VERKRUIJSSE, H.: Preparative polar organometallic chemistry 1. Springer-Verlag Publ Berlin Heidelberg New York London Paris Tokyo, 1, 1987.

BREIVOGEL, C. S., GRIFFIN, G., DI MARZO, V., AND MARTIN, B. R.: Evidence for a new G protein-coupled cannabinoid receptor in mouse brain. Mol. Pharmacol. 60 (1): 155–63., 2001.

BROWN, C. A.: Facile Reaction of potassium hydride with ketones. Rapid quantitative formation of potassium enolates from ketones via kaliation. J. Org. Chem. 39:1324, 1974.

CALLEN, J. E., DORNFELD, C. A., AND COLEMAN, G. H.: Organic Synthesis 3, 1955.

CAMPAIGNE, E. AND ARCHER, W. L.: in Org. Synth. (Eds.), Vol. II, pp 331 1963.

CAMUS, P., MARTINEZ, S., AND RINALDI, M.: Pyrazolecarboxylic acid derivatives, their preparation, pharmaceutical compositions containing them. In PCT Int. Appl., pp. 34 pp., (Sanofi-Synthelabo, Fr.; Barth, Francis)., WO, 2000.

CARPINO, L. A.; SANTILLI, A. A.; MURRAY, R. W.: Oxidative reactions of hydrazines. V. Synthesis of Monobenzyl 1,1-Disubstituted Hydrazines and 2-Amino-2,3,-dihydro-1H-benz[de]isoquinoline. J. Am. Chem. Soc., 82: 2728–2731, 1960.

CASELLAS, P., MONSIF, BOUABOULA, M., CALANDRA, B., CANAT, X., CARAYON, P., DEROCQ, J.-M., Dussossoy, D., GALIEGUE, S., MARCHAND, J., POINOT-CHAZEL, C., RINALDI-CARMONA, M., SHIRE, D. AND LE FUR, G.: Study of the distribution of peripheral cannabinoid receptor (CB2) and of the signaling pathway associated with CB2 stimulation. International Cannabis Research Society abstract, 1996.

CHANDLER, C. E., HICKMAN, M. A., LUNDY, K. M., AND MORGAN, B. P.: Use of apo B secretion/MTP inhibitors for reducing intestinal fat absorption. In Eur. Pat. Appl., pp. 23 pp., (Pfizer Products Inc., USA)., EP, 2001.

CHEN, J. P., PAREDES, W., LI, J., SMITH, D., LOWINSON, J. AND GARDNER, E. L.: □9-THC produces naloxone-blockable enhancement of presynaptic basal dopamine efflux in nucleus accumbens of conscious, freely-moving rats as measured by intracerebral microdialysis. Psychopharmacology 102:156–62, 1990.

CHEN, J., MARMUR, R., PULLES, A., PAREDES, W. AND GARDNER, E. L.: Ventral tegmental microinjection of $\Delta^9$-THC enhances ventral tegmental somatodendritic dopamine levels but not forebrain dopamine levels: evidence for local neural action by marijuana's psychoactive ingredient. Brain Res. 621:65–70, 1993.

CHENG, Y.-C. AND PRUSOFF, W. H.: Relationship between the inhibition constant (Ki) and the concentration of inhibitor which causes 50 percent inhibition (I50) on an enzymatic reaction. Biochem. Pharmacol. 22:3099–3108, 1973.

CHENG, S.-F., LIN, C.-S., AND Liu, L. K.: J. Chin. Chem. Soc. 44: 309–313, 1997.

CHILDERS, S. R. AND DEADWYLER, S. A.: Role of cyclic AMP in the actions of cannabinoid receptors. Biochem. Pharmacol. 52:819–27, 1996.

COLLINS, D. R., PERTWEE, R. G. AND DAVIES, S. N.: Prevention by the cannabinoid antagonist, SR141716A, of the cannabinoid-mediated blockade of long-term potentiation in the rat hippocampal slice. Brit. J. Pharmacol. 115:869–870, 1995.

COLQUHOUN, D.: Lectures on Biostatistics, Oxford University Press, Oxford, 1971.

COMELLI, C., DELLA VALLE, F., DELLA VALLE, M. F., AND MARCOLONGO, G.: Preparation of derivatives of alkanolamides of monocarboxylic and dicarboxylic acids as antagonists of the CB2 cannabinoid receptor. In PCT Int. Appl., pp. 78 pp., (Innovet Italia S.r.L., Italy)., WO, 2001.

COMPTON, D. R., PRESCOTR, W. R. JR., MARTIN, B. R., SIEGEL, C., GORDON, P. M. AND RAZDAN R. K.: Synthesis and pharmacological evaluation of ether and related analogues of $\Delta^8$-, $\Delta^9$-, and $\Delta^{9,11}$-tetrahydrocannabinol. J. Med. Chem. 34:3310–3316, 1991.

COMPTON, D. R., GOLD, L. H., WARD, S. J., BALSTER, R. L. AND MARTIN B. R.: Aminoalkylindole analogs: cannabimimetic activity of a class of compounds structurally distinct from $\Delta^9$-THC. J. Pharmacol. Exp. Ther. 263:1118–1126, 1992.

COMPTON, D. R., RICE, K. C., DE COSTA, B. R., RAZDAN, R. K., MELVIN, L. S., JOHNSON, M. R. AND MARTIN, B. R.: Cannabinoid structure-activity relationships: correlation of receptor binding and in vivo activities. J. Pharmacol. Exp. Ther. 265:218–26, 1993.

COMPTON, D. R., ACETO, M. D., LOWE, J. AND MARTIN, B. R.: In vivo characterization of a specific cannabinoid receptor antagonist (SR141716A): inhibition of $\Delta^9$-THC-induced responses and apparent agonist activity. J. Pharmacol. Exp. Ther. 277:586–594, 1996.

CONNORS, R. E., PAVLIK, J. W., BURNS, D. S., AND KURZWEIL, E. M.: A theoretical investigation of the pyrazole phototransposition. J. Org. Chem. 56: 6321–6, 1991.

CONWAY, T. T., BELLEAU, B. R., DOYLE, T. W., AND LUH, B. Y.:. In Brittish Patent, 1979.

CRAMER, RICHARD D. III.: Partial Least Squares (PLS): Its strengths and limitations. In: Perspectives in Drug Design, ESCOM, Leiden, pp. 269–277, 1993.

CULLINAN, G. J., FAHEY, K. J., AND KOPPEL, G. A.: Benzo[b]furan and benzo[b]thiophene derivatives useful as cannabinoid receptor antagonists. In U.S., pp. 13 pp. Cont.-in-part of U.S. Ser. No. 275,895, abandoned., (Eli Lilly and Company, USA)., US, 1997.

DEUTSCH, D. G. AND CHLN, S. A.: Enzymatic synthesis and degradation of anandamide, a cannabinoid receptor agonist. Biochem. Pharmacol. 46:791–796, 1993.

DEVANE, W. A., DYSARZ, F. A. II, JOHNSON, M. R., MELVIN, L. S. AND HOWLETT, A. C.: Determination and characterization of a cannabinoid receptor in rat brain. Mol. Pharmacol., 34:605–613, 1988.

DEVANE, W. A., HANUS, L., BREUER, A., PERTWEE, R. G., STEVENSON, L. A., GRIFFIN, G., GIBSON, D., MANDELBAUM, A., EAGER, A. AND MECHOULAM, R.: Isolation and structure of a brain constituent that binds to the cannabinoid receptor [see comments]. Science 258:1946–1949, 1992a.

DEVANE, W. A., BREUER, A., SHESKIN, T., JARBE, T. U. C., EISEN, M. S., AND MECHOULAM, R.: A novel probe for the cannabinoid receptor. J. Med. Chem. 35(11) :2065–9, 1992b.

DEWEY, W. L.: Cannabinoid pharmacology. Pharmacol. Rev. 38:151–78, 1986.

DEWEY, W. L., HARRIS, L. S., HOWES, J. F. AND NUITE, J. A.: The effect of various neurohumoral modulators on the activity of morphine and the narcotic antagonists in the tail-flick and phenylquinone tests, J. Pharmacol. Exp. Ther. 175:435–442, 1970.

DEWEY, W. L. AND HARRIS, L. S.: Antinociceptive activity of the narcotic antagonist analgesics and antagonistic activity of narcotic analgesics in rodents, J. Pharmacol. Exp. Ther. 179:652–659, 1971.

DI MARZO, V., MELCK, D., ORLANDO, P., BISOGNO, T., ZAGOORY, O., BIFULCO, M., VOGEL, Z., AND DE PETROCELLIS, L.: Palmitoylethanolamide inhibits the expression of fatty acid amide hydrolase and enhances the anti-proliferative effect of anandamide in human breast cancer cells. Biochem. J. 358: 249–55., 2001.

DRUMMOND, J., JOHNSON, G., NICKELL, D. G., ORTWINE, D. F., BRUNS, R. F., AND WELBAUM, B.: J. Med. Chem. 32 (9): 2116–2128, 1989.

DUTTA, A. K., SARD, H., RYAN, W., RAZDAN, R. K., COMPTON, D. R. AND MARTIN, B. R.: The synthesis and pharmacological evaluation of the cannabinoid antagonist SR141716A. Med. Chem. Res. 5:54–62, 1995.

EISSENSTAT, M. A., BELL, M. R., TE, D. A., ALEXANDER, E. J., DAUM, S. J., ACKERMAN, J. H., GRUETT, M. D., KUMAR, V., ESTEP, K. G., OLEFIROWICZ, E. M. ET AL.: Aminoalkylindoles: structure-activity relationships of novel cannabinoid mimetics. J. Med. Chem. 38:3094–105, 1995.

FAHEY, K. J., KOPPEL, G. A., AND CULLINAN, G. J.: Arylbenzo[b]thiophene and benzo[b]furan compds for cannabinoid receptor antagonists, their preparation, their activity, and pharmaceutical formulations containing them. In PCT Int. Appl., pp. 44 pp., (Lilly, Eli, and Co., USA)., WO, 1996.

FELDER, C. C., JOYCE, K. E., BRILEY, E. M., MANSOURI, J., MACKIE, K., BLOND, O., LAI, Y., MA, A. L. AND MITCHELL, L.: Comparison of the pharmacology and signal transduction of the human cannabinoid CB1 and CB2 receptors. Mol. Pharmacol., 48:443–450, 1995.

FERNANDO, S. R., STEVENSON, L. A., HILL, W. A., LAN, R., MAKRIYANNIS, A. AND PERTWEE, R.: Structure-activity relationships of some novel analogues of SR141716A. International Cannabis Research Society abstract, 1996.

FONG T. M., Yu, H., CASCIERI, M. A., UNDERWOOD, D., SWAIN, C. J. AND STRADER C. D.: The role of histidine 265 in antagonist binding to the neurokinin-1 receptor. J. Biol. Chem. 269:2728–2732, 1994.

GALIEGUE, S., MARY, S., MARCHAND, J., Dussossoy, D., CARRIERE, D., CARAYON, P., BOUABOULA, M., SHIRE, D., LE FUR, G. AND CASELLAS, P.: Expression of central and peripheral cannabinoid receptors in human immune tissues and leukocyte subpopulations. Eur. J. Biochem. 232:54–61, 1995.

GATLEY, S. J., GIFFORD, A. N., VOLKOW, N. D., LAU, R. AND MAKRIYANNIS, A.: [$^{123}$I]-labeled AM251: a radioligand which binds in vivo to mouse brain cannabinoid CB1 receptors. Eur. J. Pharmacol. 307:331–338, 1996.

GHALI, N. I.; VENTON, D. L.; HUNG, S. C.; LE BRETON, G. C.: A High-Yielding Synthesis of Monoalkyl Hydrazines. J. Org. Chem., 46: 5413–5414, 1981.

GOLD, L. H., BALSTER, R. L., BARRETT, R. L., BRITT, D. T. AND MARTIN, B. R.: A comparison of the discriminative stimulus properties of $\Delta^9$-THC and CP 55,940 in rats and rhesus monkeys. J. Pharmacol. Exp. Ther. 262:479–486, 1992.

GRIMMETT, M. R.: Imidazoles and their Benzo Derivatives: (iii) Synthesis and Applications. In, Comprehensive Heterocyclic Chemistry, ed. by A. R. Katritzky and C. W. Rees, vol. 5, pp. 457, Pergamon Press, Oxford, 1984.

GRIMMETT, M. R.: Imidazole and Benzimidazole Synthesis, Academic Press, 1997.

GRIMSHAW, J., AND HEWITT, S. A.: Electrochemical reactions. Part 25. A comparison of the reductive and photochemical cyclization of some i-(2-chlorophenyl)-j-phenyltriazoles. Proc. R. Ir. Acad., Sect. B 83 B (1–16): 93–101, 1983.

Guo, Y., ABADJI, V., MORSE, K. L., FOURNIER, D. J., XIUYAN, L., AND MAIRYANNIS, A.: (−)-11-Hydroxy-7′-isothiocyanato-1′,1′-dimethylheptyl-$\Delta^8$-THC: A novel, high affinity cannabinoid receptor in the brain. J. Med. Chem. 37(23):3867–70, 1994.

HAN, Y., AND HU, H.: Synthesis 1990: 122, 1990.

HAN, Y. I., AND HU, H.: Tetrahedron Lett. 30: 5285, 1989.

HANASAKI, K., MURASHI, T., AND KAI, H.: Preparation of 2-imino-1,3-thiazine derivatives as CB2R antagonists. In PCT Int. Appl., pp. 158 pp., (Shionogi & Co., Ltd., Japan)., WO, 2001.

HERKENHAM, M., LYNN, A. B., LITTLE, M. D., JOHNSON, M. R., MELVIN, L. S., DE COSTA, B. R. AND RICE, K. C.: Cannabinoid receptor localization in brain. Proc. Natl. Acad. Sci. 87:1932–1936, 1990.

HERKENHAM, M.: Cannabinoid receptor localization in brain: relationship to motor and reward systems. Ann. N.Y. Acad. Sci. 654:19–32, 1992.

HICKMAN, M. A., LUNDY, K. M., AND MORGAN, B. P.: Use of apo B secretion/MTP inhibitors as antiobesity agents. In Eur. Pat. Appl., pp. 22 pp., (Pfizer Products Inc., USA)., EP, 2001.

HILTUNEN, A. J. AND JARBE, T. U.: Cannabidiol attenuates $\Delta^9$-THC-like discriminative stimulus effects of cannabinol. Eur. J. Pharmacol. 125:301–304, 1986.

HIRST, R. A., ALMOND, S. L. AND LAMBERT, D. G.: Characterisation of the rat cerebella CB1 receptor using SR141716A, a central cannabinoid receptor antagonist. Neurosci. Lett. 220:101–104, 1996.

HOUSTON, D. B., LAN, R., PIGG, J. J., WILKEN, G., HOWLETT, A. C. AND MAKRIYANNIS, A.: Structure-activity relationship of pyrazole compounds to CB1 receptor affinity and function. International Cannabis Research Society abstract, to be presented June, 1997.

HOWLETT, A. C., JOHNSON, M. R., MELVIN, L. S. AND MILNE, G. M.: Nonclassical cannabinoid analgetics inhibit adenylate cyclase: development of a cannabinoid receptor model. Mol. Pharmacol. 33:297–302, 1988.

HUESTIS, M. A., GORELICK, D. A., HEISHMAN, S. J., PRESTON, K. L., NELSON, R. A., MOOLCHAN, E. T., AND FRANK, R. A.: Blockade of effects of smoked marijuana by the CB1-selective cannabinoid receptor antagonist SR141716. Arch. Gen. Psychiatry 58 (4): 322–8., 2001.

HUFFMAN, J. W., YU, S., SHOWALTER, V., ABOOD, M. E., WILEY, J. W., COMPTON, D. R., MARTIN, B. R., BRAMBLETT, R. D. AND, REGGIO, P. H.: Synthesis and pharmacology of a very potent cannabinoid lacking a phenolic hydroxyl with high affinity for the CB2 receptor. J. Med. Chem. 39(20):3875–3877, 1996.

HUNTER, T. R., MERICLE, J. M., PATEL, M. J. AND REGGIO, P. H. The aminoalylindole binding site at the cannabinoid CB1 and CB2 receptors. International Cannabis Research Society abstract, 1996.

INABA, T., KAYA, T., AND IWAMURA, H.: Preparation of 2-oxo-1,2-dihydroquinoline-2-carboxamide compounds as agonists and antagonists of cannabinoid receptor. In PCT Int. Appl., pp. 36 pp., (Japan Tobacco Inc., Japan)., WO, 1999.

IORIO, M. A., AND LANDI-VITTORY, R.: Farnaco Ed. Sci. 18:453–464, 1963.

ISHAC, E. J., JIANG, L., LAKE, K. D., VARGA, K., ABOOD, M. E. AND KUNOS, G.: Inhibition of exocytotic noradrenaline release by presynaptic cannabinoid CB1 receptors on peripheral sympathetic nerves. Br. J. Pharmacol. 118:2023–8, 1996.

JANSEN, E. M., HAYCOCK, D. A., WARD, S. J. AND SEYBOLD, V. S.: Distribution of cannabinoid receptors in rat brain determined with aminoalkylindoles. Brain Res. 575:93–102, 1992.

JOHNSON, M. R. AND MELVIN, L. S. The discovery of nonclassical cannabinoid analgetics. In Cannabinoids as Therapeutic Agents, CRC Press, Boca Raton, Fla., pp. 121–145, 1986.

JONES, R. G. AND. GILMAN, H.: The halogen-metal interconversion reaction with organolithium compounds. Organic Reactions 6, ch. 7, 339, 1951.

JUNG, M. E., AND HATFIELD, G. L.: Tetrahedron Lett.: 4483, 1978.

KANG, H.-Y., AND SONG, S.-E.: Tetrahedron Lett. 41: 937–939, 2000.

KAMINSKY, N. E.: Personal communication, Apr. 28, 1997.

KEIMOWITZ, A. R., MARTIN, B. R., RAZDAN, R. K., CROCKER, P. J., MASCARELLA, S. W., AND THOMAS, B. F.: QSAR analysis of $\Delta^8$-THC analogues: relationship of side-chain conformation to cannabinoid receptor affinity and pharmacological potency. J. Med. Chem. 43 (1): 59–70., 2000.

KENAKIN, T.: Pharmacologic Analysis of Drug Receptor Interaction, Raven Press, New York, pp. 324, 1993.

KENAKIN, T. The classification of seven transmembrane receptors in recombinant expression systems. Pharmacol. Rev. 48:413–463.

KORNETSKY, C.: Brain-stimulation reward: a model for the neuronal bases for drug-induced euphoria. NIDA Res. Monogr. 62:30–50,1985.

KUSTER, J. E., STEVENSON, J. I., WARD, S. J., D'AMBRA, T. E. AND HAYCOCK, D. A.: Aminoalkylindole binding in rat cerebellum: selective displacement by natural and synthetic cannabinoids. J. Pharmacol. Exp. Ther. 264:1352–1363, 1993.

LALLEMAND, F., SOUBRIE, P. H., AND DE WITTE, P. H.: Effects of CB1 cannabinoid receptor blockade on ethanol preference after chronic ethanol administration. Alcohol Clin Exp Res 25 (9): 1317–23., 2001.

LAN, R., LIU, Q., FAN, P., LIN, S., FERNANDO, S. R., MCCALLION, D., PERTWEE, R., AND MAKRIYANNIS, A.: Structure-activity relationships of pyrazole derivatives as cannabinoid receptor antagonists. Journal of Medicinal Chemistry 42 (4): 769–776, 1999.

LANGE, J. H. M., KRUSE, C. G., TIPKER, J., TULP, M. T. M., AND VAN VLIET, B. J.: 4,5-Dihydro-1H-pyrazole derivatives having CB1-antagonistic activity. In PCT Int. Appl., pp. 29 pp., (Solvay Pharmaceuticals B.V., Neth.)., WO, 2001.

LANGLEY, W. D.: Organic Synthesis Volume 1, 1932.

LEDENT, C., VALVERDE, O., Cossu, G., PETITET, F., AUBERT, J. F., BESLOT, F., BOHME, G. A., IMPERATO, A., PEDRAZZINI, T., ROQUES, B. P., VASSART, G., FRATFA, W., AND PARMENTIER, M.: Unresponsiveness to cannabinoids and reduced addictive effects of opiates in CB1 receptor knockout mice. Science 283 (5400): 401–4., 1999.

LEE, H. B., AND BALASUBRAMANIAN, S.: Solid Phase Synthesis of N-Alkyl-N-(beta-keto)amides and 1,2,4,5-Tetrasubstituted Imidazoles Using a Traceless Cleavage Strategy. Org. Lett. 2 (3): 323–326, 2000.

LE FUR, G., ARNON, M., RINALDI-CARMONI, M., BARTH, F. AND HESHMATI, H.: SR141716A, a selective antagonist of CB1 receptors and obesity. Presented at the 2001 meeting of the International Cannabinoid Research Society, Madrid, Spain, 2001.

LEE, R. A., MCANDREWS, C., PATEL, K. M., AND REUSCH, W.: Tetrahedron Lett. 965, 1973.

LICHTMAN, A. H., DIMEN, K. R. AND MARTIN, B. R.: Systemic or intrahippocampal cannabinoid administration impairs spatial memory in rats. Psychopharmacology 119:282–90, 1995.

LICHTMAN, A. H. AND MARTIN, B. R.: $\Delta^9$-THC impairs spatial memory through a cannabinoid receptor mechanism. Psychopharmacology. 126:125–131, 1996.

LYNN, A. B. AND HERKENHAM, M.: Localization of cannabinoid receptors and nonsaturable high-density cannabinoid binding sites in peripheral tissues of the rat: implications for receptor-mediated immune modulation by cannabinoids. J. Pharmacol. Exp. Ther. 268:1612–23, 1994.

MANSBACH, R. S., ROVETTI, C. C., WINSTON, E. N. AND LOWE, J. A. In: Effects of the cannabinoid CB1 receptor antagonist SR141716A on the behavior of pigeons and rats. Psychopharmacology 124:315–322, 1996.

MARTIN, B. R.: Cellular effects of cannabinoids. Pharmacol. Rev. 38:45–74, 1986.

MARTIN, B. R., COMPTON, D. R., SEMUS, S. F., LIN, S., MARCINIAK, G., GRZYBOWSKA, J., CHARALAMBOUS, A. AND MAKRIYANNIS, A.: Pharmacological evaluation of iodo and nitro analogs of $\Delta^8$-THC and $\Delta^9$-THC. Pharmacol. Biochem. Behav. 46:295–301, 1993.

MARTIN, B. R., THOMAS, B. F. AND RAZDAN, R. K.: Structural requirements for cannabinoid receptor probes. In: Cannabinoid Receptors (R. Pertwee, ed.), Academic Press, New York, N.Y., pp. 1–34, 1995a.

MARTIN, B. R., COMPTON, D. R., PRESCOTT, W. R., BARRETT, R. L., AND RAZDAN, R. K.: Pharmacological evaluation of dimethylheptyl analogs of delta 9-THC: Reassessment of the putative three-point cannabinoid-receptor interaction. Drug Alcohol Depend. 37(3):231–40, 1995b.

MARUANI, J., AND SOUBRIE, P.: Use of central cannabinoid receptor antagonists for regulating appetence. In PCT Int. Appl., pp. 32 pp., (Sanofi, Fr.)., WO, 1998.

MATSUDA, L. A., LOLAIT, S. J., BROWNSTEIN, M. J., YOUNG, A. C. AND BONNER, T. I.: Structure of a cannabinoid receptor and functional expression of the cloned cDNA [see comments]. Nature 346:561–4, 1990.

MCILWAIN, AND RICHARDSON: Biochemical Journal 33: 45, 1939.

MCPHERSON, G. A.: A practical computer-based approach to the analysis of radioligand binding experimetns. Comput. Programs Biomed. 17:107–114, 1983.

MECHOULAM, R., SHANI, A., EDERLY, H. GRUMFELD, Y.: Chemical basis of hashish activity. Science, 169:611, 1970.

MECHOULAM, R., BEN-SHABAT, S., HANUS, L., LIGUMSKY, M., KAMINSKI, N. E., SCHATZ, A. R., GOPHER, A., ALMOG, S., MARTIN, B. R., COMPTON, D. R. ET AL.: Identification of an endogenous 2-monoglyceride, present in canine gut, that binds to cannabinoid receptors. Biochem. Pharmacol. 50:83–90, 1995.

MENGE, W. M. P. B., AND TIMMERMAN, H.: Substituted Imidazoles, the Key to Histaminergic Receptors, Elsevier Science B. V., 1998.

MIGNANI, S., HITFINGER, A., ACHARD, D., BOUCHARD, H., BOUQUEREL, J., CAPET, M., GRISONI, S., AND MALLERON, J.-L.: Preparation of 1-bis(aryl)methyl-3-(alkylsulfonyl) arylmethyleneazetidines as cannabinoid CB1 receptor antagonists. In PCT Int. Appl., pp. 239 pp., (Aventis Pharma S. A., Fr.)., WO, 2000.

MITTENDORF, J., DRESSEL, J., MATZKE, M., KELDENICH, J., MAULER, F., DEVRY, J., FRANZ, J., SPREYER, P., VOEHRINGER, V., SCHUMACHER, J., ROCK, M.-H., HORVATH, E., FRIEDL, A., MOHRS, K.-H., RADDATZ, S., AND JORK, R.: Preparation of aryl trifluorobutylsulfonates as CB1 receptor antagonists. In Ger. Offen., pp. 38 pp., (Bayer A.-G., Germany)., DE, 2000.

MORGAN, B. P., AND SWICK, A. G.: Methods and pharmaceutical compositions containing Apo B secretion/microsomal triglyceride transfer protein inhibitors and anti-obesity agents for the treatment of obesity. In Eur. Pat. Appl., pp. 22 pp., (Pfizer Products Inc., USA)., EP, 2001.

MUNRO, S., THOMAS, K. L. AND ABU-SHAAR, M.: Molecular characterization of a peripheral receptor for cannabinoids. Nature 365:61–65, 1993.

MUNSON, P. J. AND RODBARD, D.: LIGAND: A versatile computerized approach for characterization of ligand-binding systems. Anal. Biochem. 107:220–239, 1980.

MURRAY, W. V. AND WACHTER, M. P.: A simple regioelective synthesis of ethyl 1,5-diarylpyrazole-3-carboxylates. J. Heterocycl. Chem. 26:1389–1392, 1989.

NEGISHI, E., KING, A. O., AND OKUKADO, N.: Selective Carbon-Carbon Bond Formation via Transition Metal Catalysis. 3. A highly Selective Synthesis of Unsymmetrical Biaryls and Diarylmethanes by the Nickle- or Palladium-Catalyzed Reaction of Aryl- and Benzylzinc Derivatives with Aryl Halides. J. Org. Chem. 42: 1821–1823, 1977.

NG CHEONG TON, J. M., GERHARDT, G. A., FRIEDEMANN, M., ETGEN, A. M., ROSE, G. M., SHARPLESS, N. S., AND GARDNER, E. L.: The effects of $\Delta^9$-THC on potassium-evoked release of dopamine in the rat caudate nucleus: an in vivo electrochemical and in vivo microdialysis study. Brain Res. 451:59–68, 1988.

NICKLAUS, M. C., WANG, S., DRISCOLL, J. S. AND MILNE, G. W.: Conformational changes of small molecules binding to proteins. Bioorg. Med. Chem. 3:411–428. 1995.

NOWELL, K. W., PETTIT, D. A., CABRAL, W. A., ZIMMERMAN, H. W., JR., ABOOD, M. E., AND CABRAL, G. A.: High-level expression of the human CB2 cannabinoid receptor using a baculovirus system. Biochem Pharmacol 55: 1893–905, 1998.

ONAIVI, E. S., GREEN, M. R. AND MARTIN, B. R.: Pharmacological characterization of cannabinoids in the elevated plus maze. J. PHARMACOL. Exp. THER. 253:1002–1009, 1990.

PACHECO, M., CHILDERS, S. R., ARNOLD, R., CASIANO, F. AND WARD, S. J.: Aminoalkylindoles: actions on specific G-protein-linked receptors. J. Pharmacol. Exp. Ther. 257:170–83, 1991.

PACHECO, M. A., WARD, S. J., AND CHILDERS, S. R.: Differential requirements of sodium for coupling of cannabinoid receptors to adenylyl cyclase in rat brain membranes. J. Neurochem. 62:1773–1782, 1994.

PAVLIK, J. W., CONNORS, R. E., BURNS, D. S., AND KURZWEIL, E. M.: Phototransposition chemistry of 1-phenylpyrazole. Experimental and computational studies. J. Am. Chem. Soc. 115: 7645–52, 1993.

PAVLIK, J. W., AND KURZWEIL, E. M.: Phototransposition chemistry of 1-methylpyrazole. Deuterium, methyl, and fluorine substitution. J. Org. Chem. 56: 6313–20, 1991.

PERTWEE, R. G.: The ring test: A quantitative method for assessing the 'cataleptic' effect of cannabis in mice, Br. J. Pharmacol., 46:753–763, 1972.

PERTWEE, R. G., STEVENSON, L. A., ELRICK, D. B., MECHOULAM, R. AND CORBETT, A. D.: Inhibitory effects of certain enantiomeric cannabinoids in the mouse vas deferens and the myenteric plexus preparation of guinea-pig small intestine, Br. J. Pharmacol. 105:980–984, 1992.

PERTWEE, R. G.; STEVENSON, L. A. AND GRIFFIN, G.: Cross-tolerance Between $\Delta^9$-THC and the Cannabimimetic Agents CP 55,940, WIN 55,212–2 and Anandainide, Br. J. Pharmacol. 110:1483–1490, 1993.

PERTWEE, R. G. AND GRIFFIN, G.: A preliminary investigation of the mechanisms underlying cannabinoid tolerance in the mouse vas deferens. Eur. J. Pharmacol. 272:67–72, 1995.

PERTWEE, R. G., GRIFFIN, G., FERNANDO, S., LI, X., HILL, A. AND MAKRIYANNIS, A.: AM630, a competitive cannabinoid receptor antagonist. Life Sci. 56:1949–1955, 1995a.

PERTWEE, R. G.: Pharmacological, physiological and clinical implications of the discovery of cannabinoid receptors: an overview. In: Cannabinoid Receptors (R. Pertwee, ed.), Academic Press, New York, N.Y., pp. 1–34, 1995b.

PERTWEE, R. G., GRIFFIN, G., LAINTON, J. A. AND HUFFMAN, J. W.: Pharmacological characterization of three novel cannabinoid receptor agonists in the mouse isolated vas deferens. Eur J Pharmacol 284:241–7, 1995c.

PERTWEE, R. G., FERNANDO, S. R., GRIFFIN, G., ABADJI, V. AND MAKRIYANNIS, A.: Effect of phenylmethylsulphonyl fluoride on the potency of anandamide as an inhibitor of electrically evoked contractions in two isolated tissue preparations. Eur. J. Pharmacol. 272:73–78, 1995d.

PERTWEE, R. G., FERNANDO, S. R., NASH, J. E. AND COUTTS, A. A.: Further evidence for the presence of cannabinoid CB1 receptors in guinea-pig small intestine. Br. J. Pharmacol. 118:2199–2205, 1996.

PERTWEE, R. G. AND FERNANDO, S. R.: Evidence for the presence of cannabinoid CB1 receptors in mouse urinary bladder. Br. J. Pharmacol. 118:2053–2058, 1996.

PETITET, F., MARIN, L. AND DOBLE, A.: Biochemical and pharmacological characterization of cannabinoid binding sites using [$^3$H]SR141716A. Neuroreport 7:789–792, 1996.

POLING, J. S., ROGAWSKI, M. A., SALEM, N. AND VICINI, S.: Anandamide, an endogenous cannabinoid, inhibits Shaker-related voltage-gated K$^+$ channels. Neuropharmacology 35:983–991, 1996.

RAMBAUD, M., BAKASSE, M., DUGUAY, G., AND VILLIERAS, J.: A one-step synthesis of alkyl 2-oxo-3-alkenoates from alkenyl Grignard reagents and dialkyl oxalates. Synthesis 564–566, 1988.

RAZDAN, R. K.: Structure-activity relationships in cannabinoids. Pharmacol. Rev. 38:75–149, 1986.

REGGIO, P. H., MCGAUGHEY, G. B., ODEAR, D. F., SELTZMAN, H. H., COMPTON, D. R. AND MARTIN, B. R.: A rational search for the separation of psychoactivity and analgesia in cannabinoids. Pharmacol. Biochem. Behav. 40:479–86, 1991.

REGGIO P. H., PANU, A. M. AND MILES, S.: Characterization of a region of steric interference at the cannabinoid receptor using the active analog approach. J. Med. Chem. 36:1761–71, 1993.

REGGIO, P. H., BRAMBLETT, R. D., YUKNAVICH, H., SELTZMAN, H. H., FLEMING, D. N., FERNANDO, S. R., STEVENSON, L. A. AND PERTWEE, R. G.: The design, synthesis and testing of desoxy-CB1: further evidence for a region of steric interference at the cannabinoid receptor. Life Sci 56:2025–32, 1995.

REGGIO, P. H.: Ligand-ligand and ligand-receptor approaches to modeling the cannabinoid CB1 and CB2 receptors: achievements and challenges. Curr. Med. Chem. 6: 665–83, 1999.

RICHARDSON, J. D., AANONSEN, L. AND HARGREAVES, K. M.: SR 141716A, a cannabinoid receptor antagonist, produces hyperalgesia in untreated mice. Eur. J. Pharmacol. 319:R3–4, 1997.

RINALDI-CARMONA, M., BARTH, F., HEAULME, M., SHIRE, D., CALANDRA, B., CONGY, C., MARTINEZ, S., MARUANI, J., NELIAT, G., CAPUT, D. ET AL: SR141716A, a potent and selective antagonist of the brain cannabinoid receptor. FEBS Lett. 350:240–244, 1994.

RINALDI-CARMONA, M., BARTH, F., HEAULME, M., ALONSO, R., SHIRE, D., CONGY, C., SOUBRIE, P., BRELIERE, J. C. AND LE FUR, G.: Biochemical and pharmacologial characterisation of SR141716A, the first potent and selective brain cannabinoid receptor antagonist. Life Sci. 56: 1941–1947, 1995a.

RINALDI-CARMONA, M., PIALOT, F., REDON, E., CONGY, C., BACHY, A., BARTH, F., BRELIERE, J. C. AND LE FUR, G.: Identification and characterization of binding sites for [3H]SR141716A, a selective brain (CB1)

cannabinoid receptor antagonist. Presentation at the 1995 international Cannabis Research Society, Scottsdale, Ariz., 1995b.

RINALDI-CARMONA, M.:, personal communication, 1997.

RINALDI-CARMONA, M., BARTH, F., MILLAN, J., DEROCQ, J.-M. CASELLAS, P., CONGY, C., OUSTRIC, D., SARRAN, M., BOUABOULA, M., CALANDRA, B., PORTIER, M., SHIRE, D., BRELIERE, J.-C. AND LE FUR, G.: SR 144528, the first potent and selective antagonist of the CB2 cannabinoid receptor. J. Pharmacol. Exp. Ther. 284: 644–650, 1998.

RONALD, R. C. AND LANSINGER, J. M.: Total synthesis of frustulosin. J. Chem. Soc., Chem. Commun. 124, 1979.

ROSENTHAL, H. E.: A graphic method for the determination and presentation of binding parameters in a complex system. Anal. Biochem. 20: 525–532, 1967.

RUBINO, T., MASSI, P., VIGANO, D., FUZIO, D., AND PAROLARO, D.: Long-term treatment with SR141716A, the CB1 receptor antagonist, influences morphine withdrawal syndrome. Life Sci 66 (22): 2213–9., 2000.

SANUDO-PENA, M. C., Tsou, K., DELAY, E. R., HOHMAN, A. G., FORCE, M. AND WALKER, J. M.: Endogenous cannabinoids as an aversive or counter-rewarding system in the rat [In Process Citation]. Neurosci. Lett. 223:125–128, 1997.

SARSHAR, S., SIEV, D., AND MJALLI, A. M. M.: Imidazole libraries on solid support. Tet. Lett. 37: 835–838, 1996.

SCATCHARD, G.: The attractions of proteins for small molecules and ions. Ann. N.Y. Acad. Sci. 51, 1951.

SCHATZ, A. R., LEE, M., CONDIE, R. B., PULASKI, J. T. AND KAMINSKI, N. E.: Cannabinoid receptors CB1 and CB2: a characterization of expression and adenylate cyclase modulation within the immune system. Tox. App. Pharmacol. 142:278–287, 1997.

SCHLICKER, E., TIMM, J. AND GOTHERT, M.: Cannabinoid receptor-mediated inhibition of dopamine release in the retina. Naunyn Schmiedebergs Arch. Pharmacol. 354:791–795, 1996.

SCHMID, P. C., PARIA, B. C., KREBSBACH, R. J., SCHMID, H. H, O. AND DEY, S. K.: Changes in anandamide levels in mouse uterus are associated with uterine receptivity for embryo implantation. Proc. Natl. Acad. Sci. USA 94:4188–92, 1997.

SELLEY, D. E., STARK, S., SIM, L. J. AND CHILDERS, S. R.: Cannabinoid receptor stimulation of guanosine-5'-O-(3-[$^{35}$S]thio)triphosphate binding in rat brain membranes. Life Sci. 59:659–68, 1996.

SELTZMAN, H. H., SETZER, S. R., WILLIAMS, D. L., DEMIAN, I., WYRICK, C. D. AND PITT, C. G.: Syntheses of carnabinoid radioligands and haptens for use in radioimmunoassay and receptor site studies. In: Marihuana '84-Proceedings of the Oxford Symposium on Cannabis (D. J. Harvey, ed.), IRL Press, Oxford and Washington, D.C., p.183, 1985.

SELTZMAN, H. H., HSIEH, Y.-A., PITT, C. G. AND REGGIO, P. H.: Synthesis of rotationally restricted tetrahydrocannabinol ethers. J. Org. Chem. 56:1549, 1991.

SELTZMAN, H. H., MOODY, M. A. AND BEGUM, M. K.: Allylic substitution/rearrangement of cannabinoids with trimethylsilyl bromide. Tetrahedron Lett. 33:3443, 1992.

SELTZMAN, H. H., CARROLL, F. I., BURGESS, J. P., WYRICK, C. D. AND BURCH, D. F.: Synthesis, spectral studies and tritiation of the cannabinoid antagonist SR141716A. J. Chem. Soc., Chem. Commun. 15:1549–1550, 1995.

SELTZMAN, H. H., FLEMING, D. M., THOMAS, B. F., GILLIAM, A. F., MACALLION, D. S., PERTWEE, R. G., COMPTON, D. R. AND MARTIN, B. R.: Synthesis and pharmacological comparison of dimethylheptyl and pentyl anandamide analogs. Submitted to J. Med. Chem. May 2, 1997.

SELTZMAN, H. H., CARROLL, F. I., BURGESS, J. P., WYRICK, C. D., AND BURCH, D. F.: Tritiation of SR141716A by Metallation-Iodination-Reduction. Tritium-Proton nOe Study. J. Labelled Compd. Radiopharm. in press, 2001.

SEZER, O., HANCI, N., AND Anac, O.: Diazoaldehyde Chemistry. Part 2. Transdiazotization of beta, gamma- and beta, delta-dioxoaldehydes. Bull. Soc. Chim. Belg. 105 (5):223–226, 1996.

SHIRE, D., CARILLON, C., KAGHAD, M., CALANDRA, B., RINALDI-CARMONA, M., LE FUR, G., CAPUT, D. AND FERRARA, P.: An amino-terminal variant of the central cannabinoid receptor resulting from alternative splicing. J. Biol. Chem. 270: 3726–3731, 1995.

SHIRE, D., CALANDRA, B., DELPECH, M., DUMONT, X., KAGHAD, M., LE FUR, G., CAPUT, D., AND FERRARA, P.: Structural features of the central cannabinoid CB1 receptor involved in the binding of the specific CB1 antagonist SR 141716A. J. Biol. Chem. 271:6941–6946, 1996.

SHOWALTER, V. M., COMPTON, D. R., MARTIN, B. R. AND ABOOD, M. E.: Evaluation of binding in a transfected cell line expressing a peripheral cannabinoid receptor (CB2): Identification of cannabinoid receptor subtype selective ligands. J. Pharmacol. Exp. Ther. 278:989–999, 1996.

SIM, L. J., SELLEY, D. E., XIAO, RAND CHILDERS, S. R.: Differences in G-protein activation by $\mu$- and σ-opioid, and cannabinoid, receptors in rat striatum. Eur. J. Pharmacol. 307:97–105. 1996.

SKAPER, S. D., BURIANI, A., DAL TOSO, R., PETRELLI, L., ROMANELLO, S., FACCI, L. AND LEON, A.: The ALIAmide palmitoylethanolamide and cannabinoids, but not anandamide, are protective in a delayed postglutamate paradigm of excitotoxic death in cerebellar granule neurons. Proc. Natl. Acad. Sci. USA. 93:3984–3989, 1996.

SMITH P. B. AND MARTIN B. R.: Spinal mechanisms of $\Delta^9$-THC-induced analgesia. Brain Res. 578:8–12, 1992.

SMITH, P. B., COMPTON, D. R., WELCH, S. P., RAZDAN, R. K., MECHOULAM, R. AND MARTIN, B. R.: The pharmacological activity of anandamide, a putative endogenous cannabinoid, in mice. J. Pharmacol. Exp. Ther. 270:219–227, 1994.

SNIECKUS, V.: Directed ortho metalation. Tertiary amide and O-carbamate directors in synthetic strategies for polysubstituted aromatics. Chem. Rev. 90:879–993, 1990.

SONAWANE, H. R., BELLUR, N. S., KULKARNI, D. G., AND AYYANGAR, N. R.: Photochemical rearrangement of alpha-chloropropiophenones to alpha-arylpropanoic acids: studies on chirality transfer and synthesis of (S)-(+)-ibuprofen and (S)-(+)-ketoprofen. Tetrahedron 50(4):1243–1260, 1994.

SONG, Z. H. AND BONNER, T. I.: A lysine residue of the cannabinoid receptor is critical for receptor recognition by several agonists but not WIN 55212–2. Mol. Pharmacol. 49:891–6, 1996.

TALLARIDA, R. J. AND MURRAY, R. B.: Graded Dose-response. In: Manual of Pharmacologic Calculations, Springer-Verlag, New York, pp. 26–31, 1987.

TERRANOVA, J. P., MICHAUD, J. C., LE FUR, G. AND SOUBRIE, P.: Inhibition of long-term potentiation in rat hippocampal slices by anandamide and WIN 55212–2: reversal by SR141716 A, a selective antagonist of CB1 cannabinoid receptors. Naunyn Schmiedebergs Arch. Pharmacol. 352:576–9, 1995.

TERRANOVA, J.-P., STORME, J.-J., LAFON, N., PERIO, A., RINALDI-CARMONI, M., LE FUR, G. AND SOUBRIE, P.: Improvement of memory in rodents by the selective cannabinoid receptor antagonist, SR 141716A. Psychopharm. 126:165–172, 1996.

THIBAUT, U.: Applications of CoMFA and related 3D QSAR approaches. In: 3D QSAR In Drug Design: Theory, Methods and Applications, Kubinyi, H. (Ed.), *ESCOM*, Leiden, pp. 443–485, 1993.

THIBAUT, U., FOLKERS, G., KLEBE, G., KUBINYI, H., MERZ, A. AND ROGNAN, D.: Recommendations for CoMFA. In: 3D QSAR in Drug Design: Theory, Methods and Applications, Kubinyi, H. (Ed.), ESCOM, Leiden, pp. 443–485, 1993.

THOMAS, B. F., WEI, X. AND MARTIN, B. R.: Characterization and autoradiographic localization of the cannabinoid binding site in rat brain using [3H]11-OH-$\Delta^9$-THC-DMH. J. Pharmacol. Exp. Ther. 263:1383–1390, 1992.

THOMAS, B. R., COMPTON, D. R., MARTIN, B. R. AND SEMUS, S. F.: Modeling the cannabinoid receptor: a three-dimensional quantitative structure-activity analysis. Mol. Pharm. 40:656–665, 1991.

THOMAS, B. F., MASCARELLA, S. W., MARTIN, B. R. AND RAZDAN, R. K.: Structure-activity analysis of anandamide analogs: relationship to a cannabinoid pharmacophore. J. Med. Chem. 39:471–479, 1996.

THOMAS, B. F., GILLIAM, A. F., BURCH, D. A., ROCHE, M. J. AND SELTZMAN, H. H. Comparative receptor binding analyses of cannabinoid agonists and antagonists: further evidence for neuronal cannabinoid receptor subtypes. J. Pharm. Exp. Ther. 285 (1): 285–292, 1998.

TIUS, M. A., HILL, W. A. G., ZOU, X. L., BUSCH-PETERSEN, J., KAWAKAMI, J. K., FERNANDEZ-GARCIA, M. C., DRAKE, D. J., ABADJI, V., AND MAKRIYANNIS, A.: Classical/non-classical cannabinoid hybrids. Life Sci., 56(23/24):2007–12, 1995.

TSOU, K., PATRICK, S. L. AND WALKER, J. M.: Physical withdrawal in rats tolerant to $\Delta^9$-THC precipitated by a cannabinoid receptor antagonist. Eur. J. Pharmacol. 280:R13-R15, 1995.

TSUCKERVANIK, I. AND. TERENT'EVA, I.: J. Gen. Chem. USSR (Engl. Transl.), 11:168, 1941.

WAKEFIELD, B. J.: Organolithium methods, best synthetic methods. Academic Press, Publ, San Diego, Ch. 3, 1988.

WEINSTOCK, L. M., CURRIE, R. B., AND LOVELL, A. V.: A general one-step synthesis of alpha-keto esters. Synth. Commun. 11(12):943–946, 1981.

WESTLAKE, T. M., HOWLETT, A. C., BONNER, T. I., MATSUDA, L. A. AND HERKENHAM, M.: Cannabinoid receptor binding and messenger RNA expression in human brain: an in vitro receptor autoradiography and in situ hybridization histochemistry study of normal aged and Alzheimer's brains. Neuroscience 63:637–52, 1994.

WILEY, J. L., LOWE, J. A., BALSTER, R. L. AND MARTIN, B. R.: Antagonism of the discriminative stimulus effects of $\Delta^9$-THC in rats and rhesus monkeys. J. Pharmacol. Exp. Ther. 275:1–6. 1995.

ZHANG, C., MORAN, E. J., WOIWODE, T. F., SHORT, K. M., AND MJALLI, A. M. M.: Synthesis of Tetrasubstituted Imidazoles via alpha-(N-acyl-N-alkylamino)-beta-ketoamides on Wang Resin. Tetrahedron Lett. 37: 751–754, 1996.

Obviously, numerous modifications and variations of the present invention are possible in light of the above teachings. It is therefore to be understood that within the scope of the appended claims, the invention may be practiced otherwise than as specifically described herein.

What is claimed is:

1. A compound of formula (III)

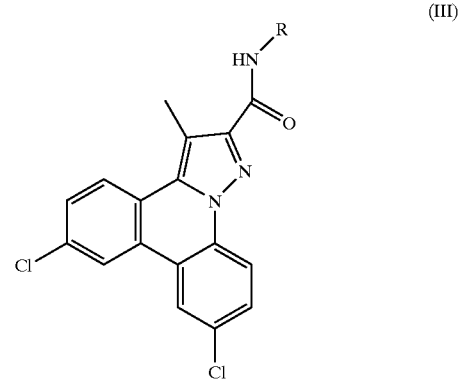

wherein R is a linear or branched hydrocarbon group having from 7 to 12 carbons, or N-piperidinyl.

2. The compound of claim 1, wherein R is a linear alkyl group.

3. The compound of claim 1, wherein R is a member selected from the group consisting of heptyl, octyl and nonyl.

4. A pharmaceutical composition, comprising:

an alkyl amide of formula (III)

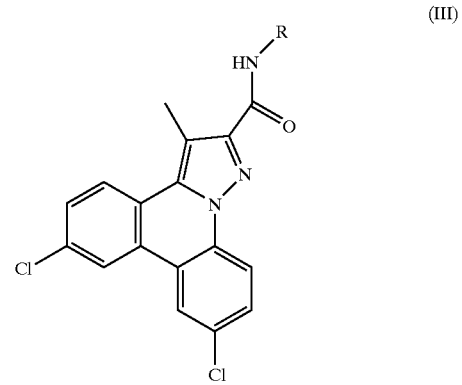

wherein R is a linear or branched hydrocarbon group having from 7 to 12 carbons, or N-piperidinyl, and a pharmaceutically acceptable carrier.

5. The pharmaceutical composition of claim 4, wherein R is a linear alkyl group.

6. The pharmaceutical composition of claim 4, wherein R is a member selected from the group consisting of heptyl, octyl and nonyl.

7. A method for the treatment of obesity, comprising:

administering to a subject in need thereof, an effective amount of an alkyl amide compound of Formula (III)

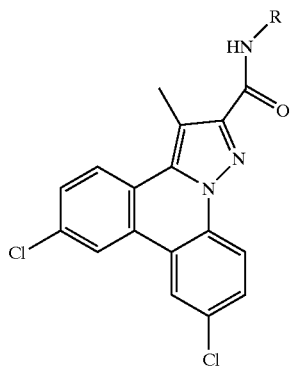

(III)

wherein R is a linear or branched hydrocarbon group having from 7 to 12 carbons, or N-piperidinyl.

8. The method of claim 7, wherein R is a linear alkyl group.

9. The method of claim 7, wherein R is a member selected from the group consisting of heptyl, octyl and nonyl.

10. The method of claim 7, wherein said effective amount is an amount of from 0.01 mg/kg to 900 mg/kg.

11. The method of claim 7, wherein said administering is performed by a method of administration selected from the group consisting of oral, intravenous, peritoneal, and nasal administration routes.

12. A compound: of formula (II)

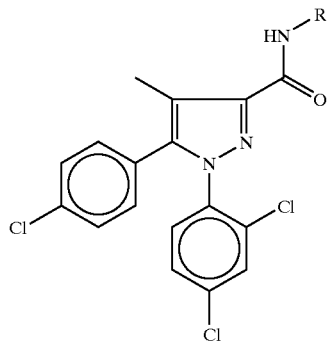

(II)

wherein R is a linear or branched hydrocarbon group having from 9 to 12 carbons.

13. The compound of claim 12, wherein R is a linear alkyl group.

14. The compound of claim 12, wherein R is nonyl.

15. A pharmaceutical composition, comprising: an alkyl amide of formula (II)

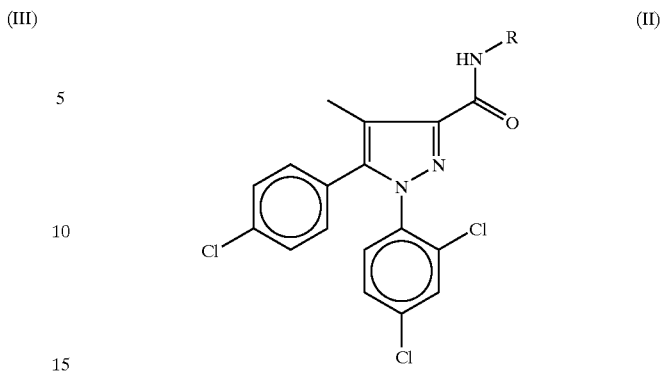

(II)

wherein R is a linear or branched hydrocarbon group having from 9 to 12 carbons, and a pharmaceutically acceptable carrier.

16. The pharmaceutical composition of claim 15, wherein R is a linear alkyl group.

17. The pharmaceutical composition of claim 15, wherein R is nonyl.

18. A method for the treatment of obesity, comprising: administering to a subject in need thereof, an effective amount of an alkyl amide compound of Formula (II) having WIN-sparing properties

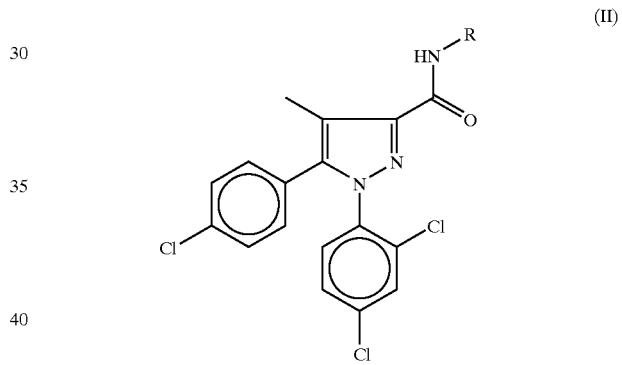

(II)

wherein R is a linear or branched hydrocarbon group having from 9 to 12 carbons.

19. The method of claim 18, wherein R is a linear alkyl group.

20. The method of claim 18, wherein R is nonyl.

21. The method of claim 18, wherein said effective amount is an amount of from 0.01 mg/kg to 900 mg/kg.

22. The method of claim 18, wherein said administering is performed by a method of administration selected from the group consisting of oral, intravenous, peritoneal, and nasal administration routes.

* * * * *